United States Patent
Morishita

(10) Patent No.: US 11,390,052 B2
(45) Date of Patent: Jul. 19, 2022

(54) STRETCHABLE MATERIAL, A MANUFACTURING METHOD OF A STRETCH MATERIAL, A STRETCHABLE MEMBER, AND A CLOTHING PRODUCT

(71) Applicant: 3M INNOVATIVE PROPERTIES COMPANY, St. Paul, MN (US)

(72) Inventor: Kenichiro Morishita, Tokyo (JP)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/733,111

(22) PCT Filed: Nov. 13, 2018

(86) PCT No.: PCT/IB2018/058917
§ 371 (c)(1),
(2) Date: May 19, 2020

(87) PCT Pub. No.: WO2019/102302
PCT Pub. Date: May 31, 2019

(65) Prior Publication Data
US 2020/0346427 A1    Nov. 5, 2020

(30) Foreign Application Priority Data
Nov. 21, 2017  (JP) .............................. JP2017-223873

(51) Int. Cl.
*B32B 3/24*        (2006.01)
*B32B 7/022*       (2019.01)
(Continued)

(52) U.S. Cl.
CPC ............ *B32B 3/266* (2013.01); *A41D 31/145* (2019.02); *A41D 31/185* (2019.02);
(Continued)

(58) Field of Classification Search
None
See application file for complete search history.

(56) References Cited

U.S. PATENT DOCUMENTS 3,655,501 A * 4/1972 Tesch ...................... B32B 27/00
                                                       428/137
3,764,450 A * 10/1973 Tesch ...................... D06C 29/00
                                                       428/137
(Continued)

FOREIGN PATENT DOCUMENTS

CN      102302400 A *  1/2012
EP      1054092 A1 * 11/2000 ............. B29C 43/28
(Continued)

OTHER PUBLICATIONS

International Search report for PCT International Application No. PCT/IB2018/058917 dated Jan. 3, 2019, 5 pages.

*Primary Examiner* — Jeffrey A Vonch

(57) ABSTRACT

A stretch material according to one embodiment is a stretch material 10 including an elastomer and having multiple discretely formed slits 15. A stretchable member includes: a stretch part having a structure in which the skin layer of the stretch material 10 is plastically deformed; and a shape retaining part by which the layer structure of the stretch material 10 is maintained. A diaper, which is one example of a clothing product, includes the stretch material 10 or the abovementioned stretchable member.

20 Claims, 12 Drawing Sheets

(51) Int. Cl.

| | |
|---|---|
| *B32B 25/08* | (2006.01) |
| *B32B 27/08* | (2006.01) |
| *B32B 27/12* | (2006.01) |
| *B32B 38/04* | (2006.01) |
| *A61F 13/49* | (2006.01) |
| *A41D 31/14* | (2019.01) |
| *A41D 31/18* | (2019.01) |
| *B32B 3/26* | (2006.01) |
| *A61F 13/15* | (2006.01) |
| *B32B 5/14* | (2006.01) |
| *B32B 7/05* | (2019.01) |
| *B32B 25/10* | (2006.01) |
| *B32B 5/02* | (2006.01) |

(52) U.S. Cl.
CPC .... *A61F 13/15707* (2013.01); *A61F 13/4902* (2013.01); *B32B 5/142* (2013.01); *B32B 7/022* (2019.01); *B32B 25/08* (2013.01); *B32B 27/08* (2013.01); *B32B 38/04* (2013.01); *A61F 2013/49022* (2013.01); *A61F 2013/49036* (2013.01); *A61F 2013/49053* (2013.01); *B32B 5/022* (2013.01); *B32B 7/05* (2019.01); *B32B 25/10* (2013.01); *B32B 2038/045* (2013.01); *B32B 2250/02* (2013.01); *B32B 2250/03* (2013.01); *B32B 2250/05* (2013.01); *B32B 2250/24* (2013.01); *B32B 2274/00* (2013.01); *B32B 2307/50* (2013.01); *B32B 2307/51* (2013.01); *B32B 2307/54* (2013.01); *B32B 2307/5825* (2013.01); *B32B 2307/734* (2013.01); *B32B 2437/00* (2013.01); *B32B 2555/02* (2013.01); *Y10T 428/2495* (2015.01); *Y10T 428/24314* (2015.01); *Y10T 428/24322* (2015.01); *Y10T 428/24331* (2015.01); *Y10T 428/24826* (2015.01); *Y10T 428/24942* (2015.01); *Y10T 442/66* (2015.04); *Y10T 442/674* (2015.04); *Y10T 442/679* (2015.04)

(56) References Cited

U.S. PATENT DOCUMENTS

| | | | | |
|---|---|---|---|---|
| 3,886,941 A * | 6/1975 | Duane | ............... | A61F 13/51305 |
| | | | | D24/126 |
| 4,591,523 A | 5/1986 | Thompson | | |
| 4,731,066 A * | 3/1988 | Korpman | .......... | A61F 13/49007 |
| | | | | 604/366 |
| 5,267,952 A * | 12/1993 | Gardner | ................ | A61F 13/062 |
| | | | | 602/41 |
| 5,536,555 A * | 7/1996 | Zelazoski | ............... | B32B 3/266 |
| | | | | 428/152 |
| 5,571,096 A | 11/1996 | Dobrin | | |
| 5,628,856 A | 5/1997 | Dobrin | | |
| 5,681,301 A | 10/1997 | Yang | | |
| 5,773,374 A * | 6/1998 | Wood | ...................... | B29C 48/22 |
| | | | | 442/328 |
| 5,804,021 A * | 9/1998 | Abuto | .................. | B32B 27/40 |
| | | | | 428/152 |
| 5,873,868 A * | 2/1999 | Nakahata | .............. | A61F 13/495 |
| | | | | 604/383 |
| 6,159,584 A * | 12/2000 | Eaton | ....................... | B32B 7/08 |
| | | | | 442/398 |
| 6,262,331 B1 * | 7/2001 | Nakahata | ............... | A61F 13/531 |
| | | | | 604/383 |
| 6,299,505 B1 * | 10/2001 | Huang | .................... | A41C 3/144 |
| | | | | 450/57 |
| 7,507,680 B2 | 3/2009 | Middlesworth | | |
| 8,304,355 B2 | 11/2012 | Baldauf | | |
| 2001/0008676 A1 * | 7/2001 | Pelkie | .................. | B29D 7/01 |
| | | | | 428/136 |
| 2002/0026171 A1 * | 2/2002 | Sayama | ............ | A61F 13/49011 |
| | | | | 604/385.3 |
| 2002/0103470 A1 * | 8/2002 | Molander | ......... | A61F 13/49015 |
| | | | | 604/394 |
| 2002/0165474 A1 | 11/2002 | Chiang | | |
| 2002/0165475 A1 * | 11/2002 | Chiang | .................... | B32B 1/08 |
| | | | | 602/26 |
| 2002/0182371 A1 * | 12/2002 | Soon | ..................... | A61F 13/513 |
| | | | | 428/137 |
| 2003/0022582 A1 * | 1/2003 | Cree | ....................... | B32B 25/10 |
| | | | | 442/394 |
| 2003/0114782 A1 * | 6/2003 | Chiang | .................... | B32B 3/30 |
| | | | | 602/61 |
| 2003/0124309 A1 * | 7/2003 | Hamulski | ............... | B32B 27/08 |
| | | | | 428/137 |
| 2004/0122404 A1 * | 6/2004 | Meyer | ................. | B32B 38/1875 |
| | | | | 604/385.19 |
| 2004/0147890 A1 * | 7/2004 | Nakahata | ............. | A61F 13/4902 |
| | | | | 604/383 |
| 2004/0175527 A1 * | 9/2004 | Shiota | ........................ | C09J 7/29 |
| | | | | 428/343 |
| 2004/0209042 A1 * | 10/2004 | Peacock | ................ | A61F 13/513 |
| | | | | 428/136 |
| 2004/0241389 A1 * | 12/2004 | Chung | .................... | A61F 13/51 |
| | | | | 428/131 |
| 2004/0247833 A1 | 12/2004 | Copat | | |
| 2005/0158513 A1 * | 7/2005 | Peacock | .................... | D04H 1/42 |
| | | | | 428/136 |
| 2006/0148361 A1 * | 7/2006 | Ng | ..................... | A61F 13/15707 |
| | | | | 442/394 |
| 2006/0246802 A1 * | 11/2006 | Hughes | .................... | B32B 5/26 |
| | | | | 442/268 |
| 2006/0251858 A1 * | 11/2006 | Thomas | ............... | A61F 13/51464 |
| | | | | 428/138 |
| 2007/0049894 A1 | 3/2007 | Fitts, Jr. | | |
| 2007/0135787 A1 * | 6/2007 | Raidel | ................. | A61F 13/15723 |
| | | | | 604/383 |
| 2007/0233034 A1 * | 10/2007 | Hildeberg | ......... | A61F 13/15203 |
| | | | | 604/385.24 |
| 2009/0208703 A1 * | 8/2009 | Wennerback | ........... | B32B 27/12 |
| | | | | 428/138 |
| 2009/0252915 A1 * | 10/2009 | Baldauf | ................ | A61F 13/4902 |
| | | | | 428/76 |
| 2011/0054432 A1 * | 3/2011 | Ueda | .................... | A61F 13/49011 |
| | | | | 604/385.3 |
| 2011/0160691 A1 * | 6/2011 | Ng | ......................... | B32B 27/28 |
| | | | | 264/145 |
| 2012/0128927 A1 * | 5/2012 | Tasi | ..................... | B32B 38/0032 |
| | | | | 156/229 |
| 2012/0207969 A1 * | 8/2012 | Mansfield | ............... | B32B 3/266 |
| | | | | 428/131 |
| 2012/0209230 A1 * | 8/2012 | Mansfield | ......... | A61F 13/51478 |
| | | | | 604/385.16 |
| 2012/0225257 A1 * | 9/2012 | Noda | ....................... | B32B 5/04 |
| | | | | 264/138 |
| 2012/0244412 A1 * | 9/2012 | Pascaly | ................. | H01M 50/449 |
| | | | | 429/247 |
| 2013/0022794 A1 * | 1/2013 | Ng | ....................... | A61F 13/4902 |
| | | | | 428/195.1 |
| 2015/0088088 A1 * | 3/2015 | Wade | .................. | A61F 13/4902 |
| | | | | 428/134 |
| 2015/0176303 A1 * | 6/2015 | Kuchar | .................. | B65D 65/38 |
| | | | | 428/136 |
| 2016/0200080 A1 * | 7/2016 | Muslet | ..................... | B32B 7/02 |
| | | | | 428/213 |
| 2016/0338435 A1 * | 11/2016 | Aihara | ...................... | A41D 1/08 |
| 2016/0339594 A1 * | 11/2016 | Aihara | .................... | A41D 31/14 |
| 2017/0297313 A1 * | 10/2017 | Langford | ................ | B32B 25/10 |
| 2018/0289559 A1 * | 10/2018 | Caneppele | ......... | A61F 13/0266 |
| 2019/0390024 A1 * | 12/2019 | Negi | ..................... | B32B 25/045 |

FOREIGN PATENT DOCUMENTS

| | | |
|---|---|---|
| JP | 10-043235 | 2/1998 |
| JP | 02839923 | 12/1998 |
| JP | 11291372 A * | 10/1999 |

(56) References Cited

FOREIGN PATENT DOCUMENTS

| | | | | |
|---|---|---|---|---|
| JP | 2001-009947 | | 1/2001 | |
| JP | 2002-102285 | | 4/2002 | |
| JP | 2001-030394 | | 8/2002 | |
| JP | 2003-524662 | | 8/2003 | |
| JP | 2004-000465 | | 1/2004 | |
| JP | 2004-098356 | | 4/2004 | |
| JP | 2005040235 A | * | 2/2005 | ........... A61F 13/476 |
| JP | 2006061175 A | * | 3/2006 | ........... A61F 13/476 |
| JP | 2014201023 A | * | 10/2014 | |
| JP | 2016-204625 | | 12/2016 | |
| WO | WO 2013-167746 | | 11/2013 | |
| WO | WO 2017-034030 | | 3/2017 | |
| WO | WO 2018-207130 | | 11/2018 | |

* cited by examiner

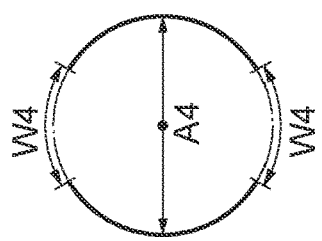
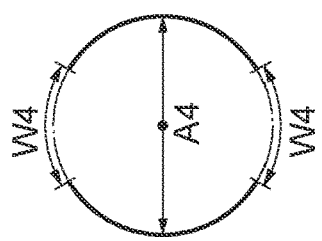
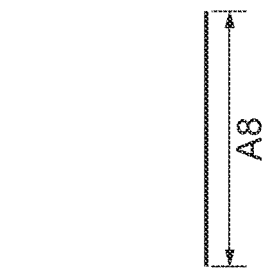
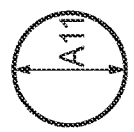
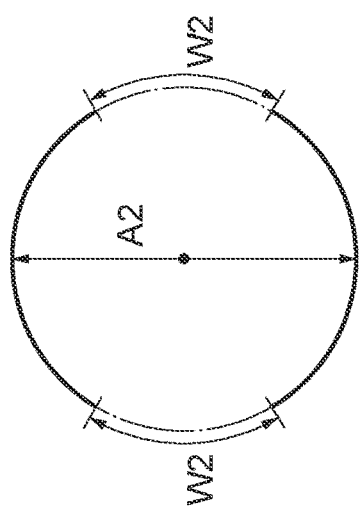
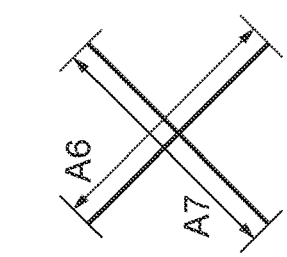
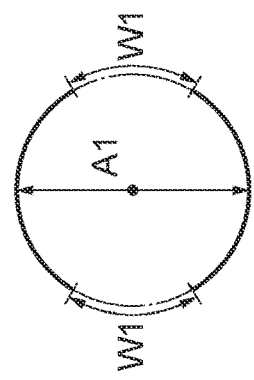
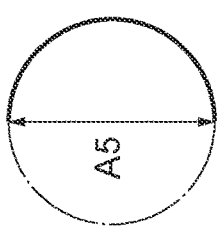
FIG. 13A  FIG. 13B  FIG. 13C  FIG. 13D
FIG. 13E  FIG. 13F  FIG. 13G  FIG. 13H
FIG. 13I  FIG. 13J

STRETCHABLE MATERIAL, A MANUFACTURING METHOD OF A STRETCH MATERIAL, A STRETCHABLE MEMBER, AND A CLOTHING PRODUCT

CROSS REFERENCE TO RELATED APPLICATIONS

This application is a national stage filing under 35 U.S.C. 371 of PCT/IB2018/058917, filed Nov. 13, 2018, which claims the benefit of Japanese Application No. 2017-223873, filed Nov. 21, 2017, the disclosure of which is incorporated by reference in its/their entirety herein.

TECHNICAL FIELD

One aspect of the present invention relates to a stretch material, a manufacturing method of a stretch material, a stretchable member, and a clothing product.

BACKGROUND

Various stretch materials and stretchable members used for clothing products, etc. have conventionally been known. For example, Patent Document 1 describes a composite material which has elasticity and air permeability and which is suitable for manufacturing an elastic diaper closing belt and an elastic side part of a diaper. The composite material includes an elastic support material which has multiple perforations and serves as a perforation film capable of being preferentially elongated in one direction.

A knitted fabric consisting of a fibrous material is pasted on both surfaces of an elastic support body. The knitted fabric is adhered to an elastic support material via an adhesive applied in a predetermined pattern. The abovementioned predetermined pattern is formed by multiple stripe orthogonally arranged in the elongation direction of the elastic support body.

The elastic support body wound in a roll is drawn from the roll, after which an adhesive is applied in the abovementioned pattern. In contrast, a knitted fabric wound in a roll is drawn from the roll, then transported in the direction crossing in the transportation direction of the elastic support body. The thus transported knitted fabric is pasted on one surface or both surfaces of the elastic support body. When the knitted fabric is pasted to the elastic support body to from a laminated composite and this laminated composite is subjected to punching, an elastic side part for a diaper capable of being elongated can be obtained.

PRIOR ART DOCUMENTS

Patent Document 1: JP 2009-241601 A

SUMMARY OF THE INVENTION

The abovementioned elastic support body is formed of multiple perforations, which are, for example, formed by high temperature rollers with needles. That is, needles pierce the elastic support body, thereby forming perforations. Because perforations are formed, permeability is enhanced in comparison with the case of no perforations.

Incidentally, if needles pierce the elastic support body to from perforations, minute projections and recesses may be formed in the elastic support body, with the minute projections and recesses capable of imparting a rough feel. The stretch material such as abovementioned elastic support body, for example, may be used for a clothing product such as diapers, etc. and is presumably used in close proximity to the human body. Therefore, a stretch material with a pleasant feel is required.

SUMMARY OF THE INVENTION

A stretch material according to one aspect of the present invention is a stretch material including an elastomer and having multiple discretely formed slits.

Because the abovementioned stretch material according to one aspect has multiple discretely formed slits, permeability can be enhanced. If perforations are formed using heated needles, the heat generates projections and recesses; in contrast, if slits are formed, minute projections and recesses tend not to be formed in the stretch material, enabling the creation of a stretch material having little roughness. If perforations are opened by die cutting to reduce projections and recesses, hole parts are pushed and cut, generating waste; in contrast, if slits are formed, the generation of such waste can be suppressed. Moreover, in the case of perforations with no slits, adhesive applied during lamination may pass through the stretch material; in contrast, if slits are formed, the passage of such an adhesive can be suppressed.

The slits may be arc-shaped. As a result, for example, if the slits are bent, when the stretch material is elongated, splits from the slits tend not to be generated.

The slits may be arc-shaped, stretching in the elongation direction. As a result, for example, when the stretch material is elongated in the elongation direction, the slits tend not to be excessively opened. Therefore, when the stretch material is elongated in the elongation direction, splits from the slits can be suppressed; accordingly, the durability of the stretch material can be enhanced when elongated in the elongation direction.

The slits may be circular arc-shaped or elliptical arc-shaped and the diameter of the slits or the length of the short axis thereof may be 0.3 mm or larger and 8 mm or smaller. As a result, for example, because the slits have a circular arc-shape or elliptical arc-shape with no corners, breaks tend not to be generated from the slits. Moreover, when the diameter of the slits or the short axis thereof is 0.3 mm or larger and 8 mm or smaller, the aesthetically pleasing appearance of the stretch material with multiple slits formed therein can be enhanced.

The stretch material may include: a core layer including an elastomer; and a skin layer provided on the primary surface of the core layer, wherein the slits may penetrate through the core layer and the skin layer. As a result, for example, because the slits penetrate through a core layer and a skin layer, a core layer and a skin layer having high permeability can be obtained.

The slits may be expanded when the stretch material is elongated. As a result, for example, because the slits are expanded during elongation of the stretch material, higher permeability can be obtained during elongation. Note that expanding is also referred to as activating.

The permeability may be 10 $(cm^3/cm^2 \cdot s)$ or higher when the slits are expanded. As a result, for example, high permeability can be obtained.

The tensile stress at second 150% elongation may be 2 N/25 mm or lower. As a result, for example, when wearing a clothing product, it can be easily elongated.

The recovery stress at second 250% elongation may be 0.2 N/25 mm or higher. As a result, for example, upon wearing, mechanical properties suitable for being fit for the human body can be obtained.

The elongation rate may be 150% or higher when it is elongated in at least one direction. As a result, for example, in the state in which multiple slits are formed, a high elongation rate can be maintained.

The tensile strength may be 1 N/25 mm or higher when it is elongated in at least one direction. As a result, for example, in the state in which multiple slits are formed, high tensile strength can be maintained.

A manufacturing method of a stretch material according to one aspect of the present invention is a manufacturing method of a stretch material including an elastomer, including: a step of forming multiple discretely formed slits by cutting the stretch material. In this manufacturing method of a stretch material, multiple discretely disposed slits are formed by cutting the stretch material. Therefore, because multiple discretely disposed slits can be formed in the stretch material, the same operational effects as in the abovementioned stretch material can be obtained.

A stretchable member according to one aspect of the present invention includes: a stretch part having a structure in which the skin layer of the abovementioned stretch material is plastically deformed; and a shape retaining part by which the layer structure of the stretch material is maintained. Because this stretchable member includes the abovementioned stretch material, the same operational effects as in the abovementioned stretch material can be obtained. Moreover, if this stretchable member is applied to the clothing product, a stretch part is elongated when worn, with the shape of a shape retaining part maintained. Therefore, because it can be bonded to other members in the shape retaining parts, favorable bondability to other members is obtained.

The clothing product according to one aspect of the present invention includes the abovementioned stretch material or the abovementioned stretchable member. In this clothing product, the same operational effects as in the abovementioned stretch material and stretchable member can be obtained.

According to one aspect of the present invention, permeability can be enhanced, providing a pleasant feel.

BRIEF DESCRIPTION OF THE DRAWINGS

FIGS. 13A to 13J are views illustrating the slits of examples as well as the through holes of reference examples.

EMBODIMENT FOR CARRYING OUT THE INVENTION

Figure 1:
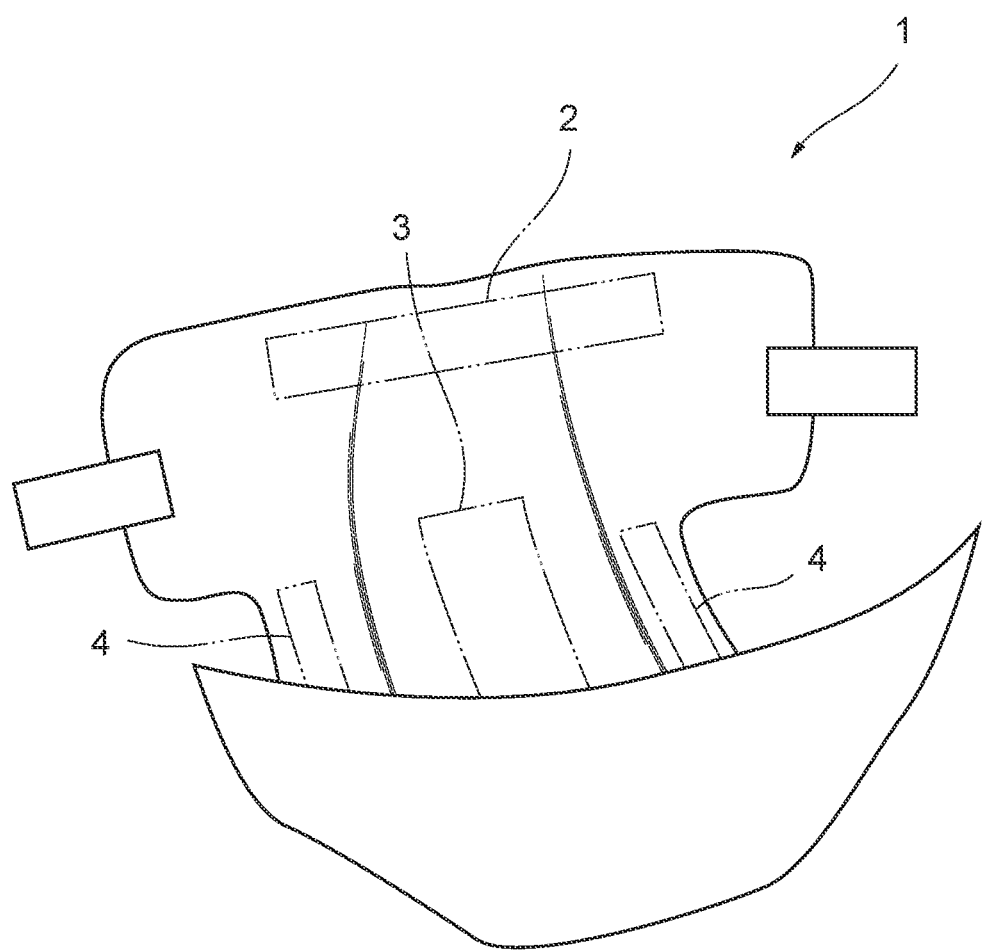
FIG. 1 is a perspective view illustrating one example of a clothing product according to an embodiment.

Hereinafter, the embodiments of the stretch material, stretchable member, and clothing product according to the present invention will be described with reference to the drawings. In the description of the drawings, the same symbols are assigned to the same or equivalent elements, with overlapping descriptions appropriately omitted. Moreover, for convenience of ease of understanding, parts of the drawings are depicted in a simplified or exaggerated manner, with the dimension ratios, etc. not limited to those described in the drawings.

Stretch Material

The stretch material according to the present embodiment includes: a core layer including an elastomer; and a skin layer having lower tensile yield stress than the core layer. When at least part of the skin layer is plastically deformed via stretching in the stretch material, a stretchable member including a stretch part is formed. In forming the stretchable member, part of the skin layer may be plastically deformed, thereby providing a part (shape retaining part) in which the layer structure of the stretch material is maintained. The stretchable member having the shape retaining part assures favorable bondability to other members in the shape retaining part.

The stretch material may have a layer structure (skin layer/core layer/skin layer) in which a skin layer is laminated on both primary surfaces of the core layer. The tensile stress on both primary surface sides is more uniform in this stretch material, preventing warpage, etc. caused by non-uniform contraction. In this stretch material, because skin layers are brought into contact with each other when wound in a roll shape, blocking between stretch materials (for example, between a skin layer and a core layer) is prevented, workability when unwound, and storage stability of the stretch material are favorable. Note that the layer structure of the stretch material is not limited to that mentioned above, and for example, may be a layer structure (core layer/skin layer) in which the skin layer is laminated on only one surface side of the core layer.

The core layer and the skin layer may be directly adhered or indirectly adhered via an intermediate layer. The intermediate layer, for example, may be a modified layer including a color material or an adhesive layer in which the core layer and the skin layer are bonded to each other. While the adhesion aspect of the core layer and the skin layer is not particularly limited, for example, resins making up the core layer and the skin layer may be fused or may be adhered via the adhesive layer interposed between the core layer and the skin layer.

While the thickness of the core layer and the thickness of the skin layer are not particularly limited, the thickness of the core layer may be the thickness of the skin layer or larger. In this case, narrowing (necking) of the stretch part during elongation can be more assuredly suppressed. Because necking during elongation can be decreased, local operation of the tightening force is prevented and excellent comfort when worn can be achieved. Moreover, if the skin layer has the below-mentioned microphase separation structure, because the core layer is thicker than the skin layer, necking is more assuredly suppressed, with comfort when worn further improved. Moreover, with the stretch material in which the skin layer has a microphase separation structure, the elongation during elongation tends to be further uniform.

In the present embodiment, the ratio of the thickness of the skin layer to the thickness of the core layer may be 0.1 or higher and 1 or lower, or may be 0.2 or higher and 0.5 or lower. In this case, necking during elongation is further assuredly suppressed. Note that when multiple skin layers are laminated in the stretch material, "the thickness of the skin layers" indicates the total thickness of each skin layer. Moreover, when multiple core layers are laminated in the stretch material, "the thickness of the core layers" indicates the total thickness of each core layer.

In the present embodiment, the tensile stress of the stretch material at 300% elongation in at least one direction in the stretch material may be 110% or lower of the tensile yield stress of the skin layer in one direction. If the tensile stress at 300% elongation is 110% or lower of the tensile yield stress of the skin layer, even when practically useful elongation of approximately 200% is carried out, the shape retaining part can maintain the original shape. Therefore, bondability to other members is further favorable, with more repeated use possible.

Note that in the present embodiment, measurements are made such that the tensile stress of the stretch material at 300% elongation is in accordance with JIS K 7127, the width of the test piece is 25 mm, the interval between chucks is 50 mm, and the speed of the test is 300 mm/min. Note that if the stretch material has multiple skin layers, the maximum tensile yield stress of each skin layer is "the tensile yield stress of the skin layer." The tensile yield stress of the skin layer may be measured by peeling the skin layer from the stretch material or measured using a test piece identical to that of the skin layer. Note that as a simple method, in the tensile stress test of the stretch material, the yield point at which all the skin layers are plastically deformed can be regarded as the tensile yield stress of the skin layer.

In the present embodiment, when the stretch material is elongated by 200% in at least one direction, the contraction percentage (the ratio of the width contracted by the elongation to the width before elongation) in the width direction orthogonal to the elongation direction may be 30% or lower, preferably 25% or lower, more preferably 15% or lower, further preferably 10% or lower.

If the stretchable member has the stretch part and the shape retaining part, the width of the shape retaining part is kept constant and the stretch part is narrowed in accordance with the elongation. In the stretch material, for example, if the contraction percentage in the width direction orthogonal to the elongation direction at 200% elongation is 30% or lower, the degree of narrowing of the stretch part is sufficiently small, with attachability and wearability capable of being sufficiently assured. This stretch material may be stretched to form the stretch part in the direction in which the contraction percentage is within the abovementioned range.

Note that in the present embodiment, the contraction percentage in the width direction orthogonal to the elongation direction at 200% elongation indicates a value measured by the following method. First, a rectangular test piece having a long side and a short side in the elongation direction and the width direction (width: 50 mm, length: 50 mm or larger) is prepared. Both ends of the test piece in the elongation direction are held so as to give a length of the stretched part of 50 mm and are stretched by 200% in the elongation direction. If the initial width of the test piece is L2, the minimum value of the width of the test piece when stretched by 200% is L1 and the contraction percentage (%) is calculated as (L2−L1/L2)×100.

Next, each layer making up the stretch material according to the present embodiment will be described.

Core Layer

The stretch material according to the present embodiment includes a core layer including an elastomer. The core layer is a layer bearing an elastic function of the stretchable member, with the composition of the core layer capable of being selected so as to have the desired rubber elasticity. The elastomer included in the core layer is a material having rubber elasticity, with the core layer, for example, having tensile stress 10% lower than the skin layer. In the present embodiment, 10% tensile stress is also referred to as 10% Modulus, which serves as the force per unit area necessary for 10% elongation, and is measured in accordance with JIS K 6251.

10% tensile stress of the core layer, for example, may be 0.5 MPa or lower, may be 0.3 MPa or lower, or may be 0.1 MPa or lower. As a result, because it follows despite the stress being small and is easily elongated, a stretchable member having excellent handleability is obtained. Moreover, the core layer may have 300% tensile stress within the abovementioned range in at least one direction. Note that the core layer may have 300% tensile stress within the abovementioned range in the stretching direction of the stretch material.

The thickness T1 of the core layer, for example, may be 10 μm or larger, preferably 15 μm or larger. The thickness T1 of the core layer, for example, may be 100 μm or smaller, 50 μm or smaller, or 35 μm or smaller, in terms of reducing material costs while obtaining sufficient effects.

The core layer may be made up of a resin material including an elastomer (hereinafter, also referred to as "resin material (A)"). Exemplary kinds of the elastomers include a styrene-isoprene-styrene block copolymer (SIS), styrene-butadiene-styrene block copolymer (SBS), styrene-ethylene/butylene-styrene block copolymer (SEBS), styrene butadiene rubber, hydrogenated or partially hydrogenated SIS, hydrogenated or partially hydrogenated SBS, polyurethane, ethylene copolymer (for example, ethylenevinylacetate, ethylene-propylene copolymer, ethylene-propylene-diene terpolymer), propylene oxide (PO), etc.

The resin material (A) may include components other than those mentioned above. For example, the resin material (A) may include a stiffening agent (for example, polyvinylstyrene, polystyrene, poly α-methylstyrene, polyester, epoxy resin, polyolefin, coumarone-indene resin), viscosity reducing agent, plasticizer, tackifier (for example, aliphatic hydrocarbon tackifier, aromatic hydrocarbon tackifier, terpene resin tackifier, hydrogenated terpene resin tackifier), dye, pigment, antioxidant, antistatic agent, adhesive, anti-tack agent, slip agent, thermal stabililizer, photostabililizer, foaming agent, glass bubbles, starch, metal salt, microfibers, etc.

Skin Layer

The skin layer according to the present embodiment, for example, has tensile stress 10% higher than the core layer in at least one direction. The skin layer functions to protect the core layer and is plastically deformed via stretching when manufacturing the stretchable member. At this time, if the core layer is elastically deformed and the skin layer is plastically deformed, the stretched part is available as the stretch part of the stretchable member. Moreover, the skin layer may function to maintain the shape of the shape retaining part in the stretchable member.

10% tensile stress of the skin layer, for example, may be 1 MPa or higher or may be 2 MPa or higher. As a result, it tends not to be deformed with small tensile stress, leading to favorable handleability of the stretch material. Moreover, 10% tensile stress of the skin layer, for example, may be 15 MPa or lower or may be 10 MPa or lower. As a result, the stress for plastically deforming the skin layer can be decreased, thereby improving processability.

Moreover, the skin layer may have 10% tensile stress within the abovementioned range in at least one direction. The skin layer may have 10% tensile stress within the abovementioned range in the stretching direction of the stretch material. Note that in the present embodiment, 10% tensile stress of the skin layer is measured in accordance with JIS K 6251.

The tensile yield stress of the skin layer, for example, may be 2 N/25 mm or higher, preferably 2.5 N/25 mm or higher, more preferably 3 N/25 mm or higher. Moreover, the tensile yield stress of the skin layer, for example, may be 10 N/25 mm or lower, preferably 7 N/25 mm or lower.

Note that the skin layer may have tensile yield stress within the abovementioned range in at least one direction. Moreover, the skin layer may have tensile yield stress within the abovementioned range in the stretching direction of the stretch material. Note that measurements are made such that the tensile yield stress of the skin layer is in accordance with JIS K 7127, the width of a test piece is 25 mm, the interval between chucks is 50 mm, and the speed of the speed is 300 mm/min.

The tensile yield strain of the skin layer, for example, may be 20% or lower, preferably 15% or lower. Note that the skin layer may have a tensile yield strain within the abovementioned range in at least one direction. Moreover, the skin layer may have a tensile yield strain within the abovementioned range in the stretching direction of the stretch material. In the present embodiment, the tensile yield strain of the skin layer is measured in accordance with JIS K 7127.

The thickness T2 of the skin layer, for example, may be 2 μm or larger, preferably 5 μm or larger, in terms of being able to easily obtain the abovementioned suitable tensile properties in addition to facilitating the manufacture thereof, etc. Moreover, the thickness T2 of the skin layer, for example, may be 30 μm or smaller, preferably 20 μm or smaller, in terms of being able to further reduce the strain of the stretch part when the elongation state is maintained for a long period of time.

In one aspect, a resin material making up the skin layer (hereinafter, also referred to as a "resin material (B)") may form the microphase separation structure. An easily plastically deformed phase structure is densely distributed over this overall skin layer, allowing it to be uniformly plastically deformed via stretching. As a result, the formed stretch part has excellent elongation uniformity during elongation. Moreover, when the skin layer has a microphase separation structure, necking during elongation is more remarkably suppressed, with a stretchable member with further excellent comfort when worn achieved.

Further, if the abovementioned skin layer is used, elongation is uniform at a relatively low degree of stretching such as 100% stretching, stretching of the stretch material can be carried out at any degree of stretching such as 100%, 150%, 200%, 250%, and 300%. Note that if the degree of stretching during stretching is different, the mechanical properties such as elasticity of the formed stretch part and tensile stress change. That is, in this aspect of changing the degree of stretching during stretching, stretch parts having different properties can be formed from the same stretch material. Therefore, for example, even if different sites of a clothing product require different properties, the same stretch material can be applied to each site by adjusting the degree of stretching in accordance with the required properties.

The microphase separation structure formed of the resin material (B), for example, may be a lamella structure, a gyroid structure, a cylinder structure, a BCC structure, etc. The microphase separation structure, for example, may be formed of a block copolymer or formed of a polymer blend.

The resin material (B) may include a block copolymer. As the block copolymer, a block copolymer forming the microphase separation structure is preferable. Exemplary block copolymers include, as elements, an olefin base such as ethylene, propylene, or butylene, an ester base such as ethylene terephthalate, a styrene base such as styrene, etc.

The resin material (B) may form the microphase separation structure by a polymer blend including two or more polymers. Exemplary polymers included in the resin material (B) include polypropylene, polyethylene, polybutylene, polyethylene terephthalate, polystyrene, etc.

In another aspect, the resin material (B) may not form the microphase separation structure but rather form a uniform layer structure. As a result, in the stretch part of the stretchable member, strain due to being worn for a long period of time can be remarkably suppressed. Moreover, when the skin layer has a uniform layer structure, strain due to the abovementioned elongation test can be easily suppressed within a suitable range of 25% or lower. That is, according to the present aspect, in comparison with the resin material (B) forming the microphase separation structure, the strain of the stretch part caused by being worn for extended periods of time can be further suppressed, while excellent fitness can be maintained for a long period of time.

The resin material (B) may include a homopolymer. According to the resin material (B) including a homopolymer, the abovementioned skin layer having a uniform layer structure can be easily obtained.

Exemplary homopolymers include polypropylene, polyethylene, polybutylene, etc.

The resin material (B) may include components other than those mentioned above. For example, a mineral oil extending agent, antistatic agent, pigment, dye, antitack agent, starch, metal salt, stabililizer, etc. may be included.

While the manufacturing method of a stretch material according to the present embodiment is not particularly limited, for example, a general multilayer film molding technique using the resin material can be applied.

In the stretch material according to the present embodiment, for example, the resin material (A) making up the core layer and the resin material (B) making up the skin layer may be simultaneously extrusion molded to integrally mold the core layer and the skin layer. The conditions of simultaneous extrusion molding may be appropriately adjusted in accordance with the compositions of the resin material (A) and the resin material (B), etc. Moreover, the stretch material according to the present embodiment may be manufactured by molding layer A including the resin material (A) and layer B including the resin material (B) and laminating layer A and layer B.

Stretchable Member

The stretchable member according to the present embodiment includes a stretch part (also referred to as an activated part) having a structure in which the skin layer of the stretch material is plastically deformed. Moreover, the stretchable member according to the present embodiment may include a shape retaining part (also referred to as an unactivated part) in which the layer structure of the stretch material is maintained.

In the stretchable member according to the present embodiment, because the stretch part functions as a rubber elastic body, it can be suitably used as an elastic web applied to a clothing product, etc. Moreover, when the stretchable member according to the present embodiment is bonded to other members in the shape retaining part, favorable bondability to other members is obtained.

Moreover, in the stretchable member, if the elongation during elongation is nonuniform, attachability as well as comfort when worn may be impaired. In the present embodiment, regarding the aspect in which the skin layer has a microphase separation structure, the stretch part may have excellent elongation uniformity.

Moreover, particularly in applying the stretchable member to a clothing product in close contact with the skin, if the width of the stretch part during elongation is small, tightening force easily locally operates and may impair comfort when worn. In the present embodiment, regarding the aspect in which the skin layer has a microphase separation structure, because the degree of narrowing of the stretch part during elongation is sufficiently small, attachability as well as comfort when worn may be sufficiently assured.

Moreover, in applying the stretchable member to the clothing product, deformation caused by repeated use thereof may be problematic. Because the stretchable member according to the present embodiment is formed of the abovementioned stretch material, the shape retaining part can maintain the original shape maintain even after repeated use and favorable bondability to other members may be maintained.

The stretch part has a structure in which the skin layer of the stretch material is plastically deformed. That is, the stretch part may include a core layer as well as a plastically deformed skin layer. In the stretch part, the plastically deformed skin layer may be present as one continuous layer or may be a layer divided by stretching.

The shape retaining part has the layer structure of the stretch material. That is, the shape retaining part may include the core layer and the skin layer. The shape retaining part can also be referred to as the nonstretched part of the stretch material.

The stretchable member is manufactured by subjecting the stretch material to stretching in accordance with the usage application thereof. While the application of the stretchable member is not particularly limited, for example, it may be used for the application of clothing. More specifically, exemplary stretchable members to be used include a disposable diaper, incontinence underwear for adults, shower cap, operation gown, hat and boots, disposable pajamas, shawl for sports, clean room clothing, hat head band, visor, ankle band, wrist band, rubber pants, wet suit, etc.

The manufacturing method of the stretchable member may include the step of stretching at least part of the stretch material and plastically deforming at least part of the skin layer (also referred to as the step of activating at least part of the stretch material). When the stretch material is stretched until the skin layer is plastically deformed, the stretch part is formed. Plastic deformation is generally achieved by stretching past the tensile yield strain of the skin layer.

In the manufacturing method of the stretchable member, only part of the skin layer may be plastically deformed to form the stretch part and the shape retaining part.

The stretching method of the stretch material is not particularly limited. For example, both ends of the stretch material are held at a predetermined width and stretched, thereby forming the stretchable member including two shape retaining parts (held nonstretched parts) having a predetermined width as well as the stretch part formed between the shape retaining parts.

The temperature conditions of the stretch material at stretch are not particularly limited and may be normal temperature. The stretching ratio of the stretch material may be the tensile yield strain of the skin layer or higher and may be a practically presumable stretching ratio or higher. Moreover, because mechanical properties of the stretch part may change in accordance with the stretching ratio, a stretching ratio in accordance with the desired properties may be used.

The clothing product includes the abovementioned stretch material or stretchable member. The clothing product, for example, may be a diaper (open type, pants type), incontinence underwear for adults, shower cap, operation gown, hat and boots, disposable pajamas, shawl for sports, clean room clothing, hat head band, visor, ankle band, wrist band, rubber pants, wet suit, etc.

Next, one aspect of the present embodiment will be described with reference to the drawings. Note that the present invention is not limited to the following aspects.

FIG. 1 is a perspective view illustrating an open type (tape type) diaper 1, which is a clothing product according to an embodiment. As illustrated in FIG. 1, the diaper 1 includes a waist part 2 contacting the waist, leg openings 3 contacting between the legs, and both side parts 4 positioned on both the right and left sides of the leg openings 3. The stretch material and stretchable member according to the present embodiment are applicable to all of the waist part 2, leg openings 3, and both side parts 4. Moreover, the stretch material and stretchable member according to the present embodiment are applicable to a leg opening of the diaper, a leg gather of the diaper, or the outer diaper, etc.

Figure 2:
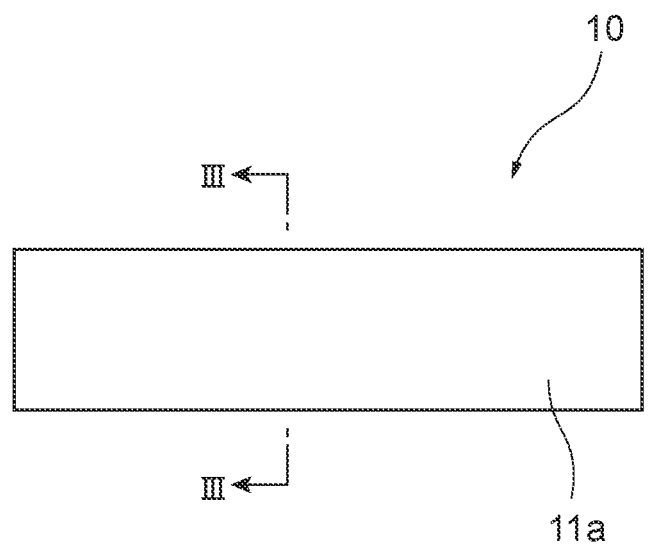
FIG. 2 is a plan view illustrating one aspect of a stretch material before a stretchable member included in the clothing product of FIG. 1 is expanded.
Figure 3:
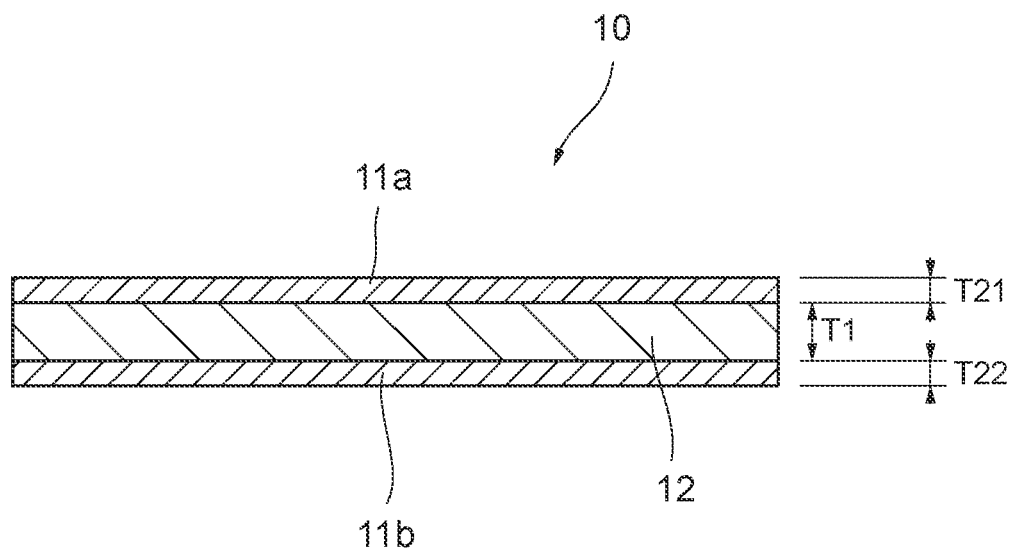
FIG. 3 is an enlarged cross-sectional view taken along line III-III of FIG. 2.

FIG. 2 is a plan view illustrating a stretch material 10 according to one aspect, while FIG. 3 is a cross-sectional view taken along line of III-III FIG. 2. As illustrated in FIGS. 2 and 3, in a plan view, the stretch material 10 has a rectangular shape. The stretch material 10 is film-shaped stretched into a planar shape. For example, an unwoven fabric is laminated on both primary surfaces of the stretch material 10 and used for the diaper 1.

The stretch material 10 has: a core layer 12; and skin layers 11a, 11b provided on both primary surfaces of the core layer 12. Both the core layer 12 and the skin layers 11a, 11b are sheet-shaped, with the skin layers 11a, 11b protecting each primary surface of the core layer 12. Note that only either one of the skin layers 11a, 11b may be provided on one primary surface of the core layer 12. The compositions of the resin material making up the skin layers 11a, 11b and the core layer 12 may be the same or different from each other.

In the stretch material 10, if the thickness of the core layer 12 is T1, the thickness of the skin layer 11a is T21, and the thickness of the skin layer 11b is T22, the thickness T1 of the core layer 12 may be the total thickness T21+T22 of the skin layers 11a, 11b or larger. The thickness T2 of the abovementioned skin layers corresponds to the total of the thickness T21 of the skin layer 11a and the thickness T22 of the skin layer 11b. The ratio of the thickness T21+T22 (thickness T2) to thickness T1, for example, is 0.1 or larger and 1 or smaller.

In the stretch material 10, the core layer 12 may be made up of a resin material containing branched polymers. The skin layers 11a, 11b may be made up of a resin material including homopolymers. In this case, even if the elongation state is maintained for a long period of time, the stretch part formed from the stretch material 10 has little strain, and if a clothing product such as the diaper 1 is applied, excellent fitness can be maintained for a long period of time.

Figure 4:
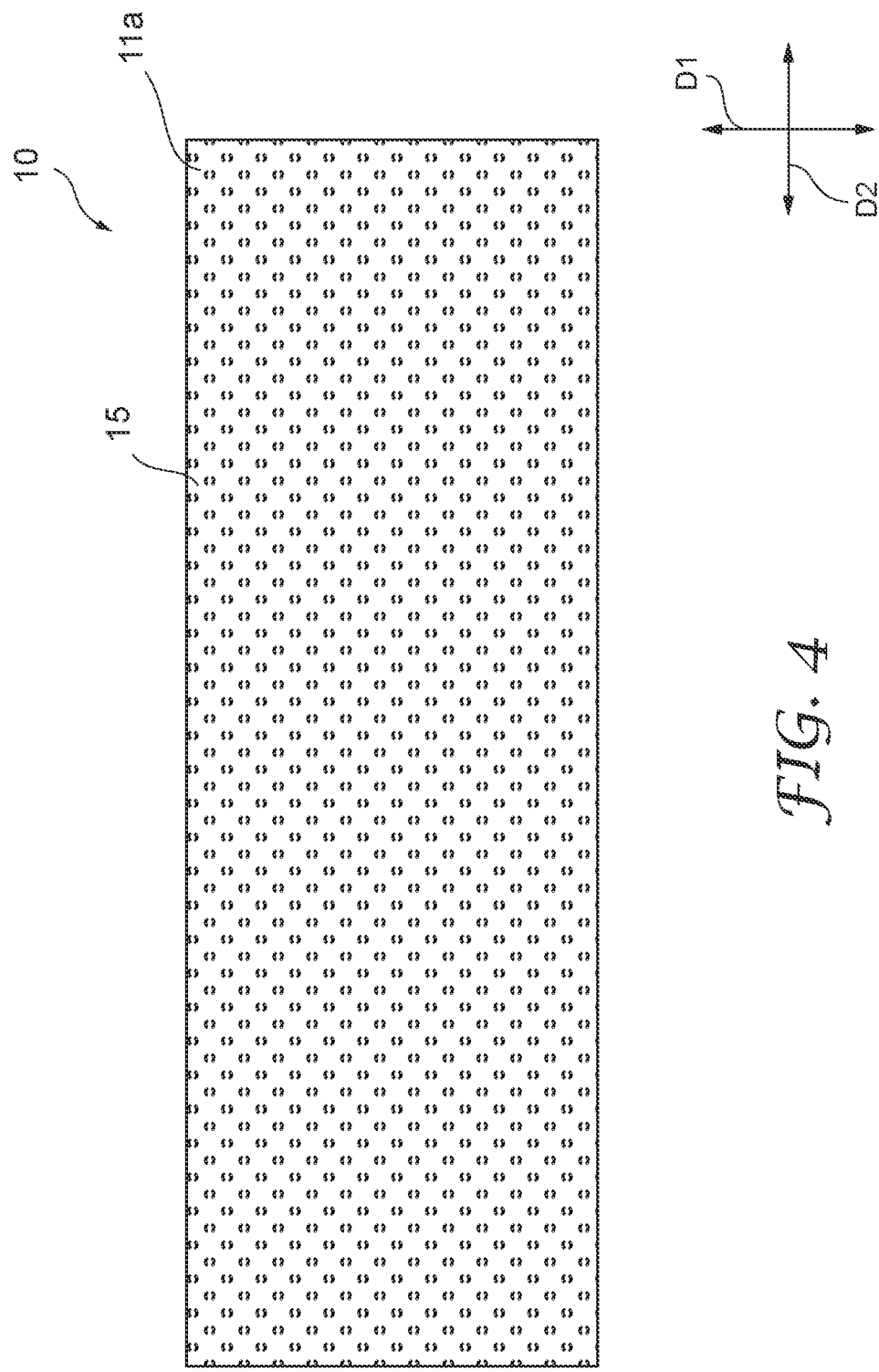
FIG. 4 is a plan view of a stretch material obtained by enlarging the plan view of FIG. 2.

FIG. 4 is a plan view obtained by enlarging the stretch material 10. As illustrated in FIG. 4, the stretch material 10 has a rectangular shape having a long side stretching in the longitudinal direction D2 as well as a short side stretching in the width direction D1.

Figure 5:
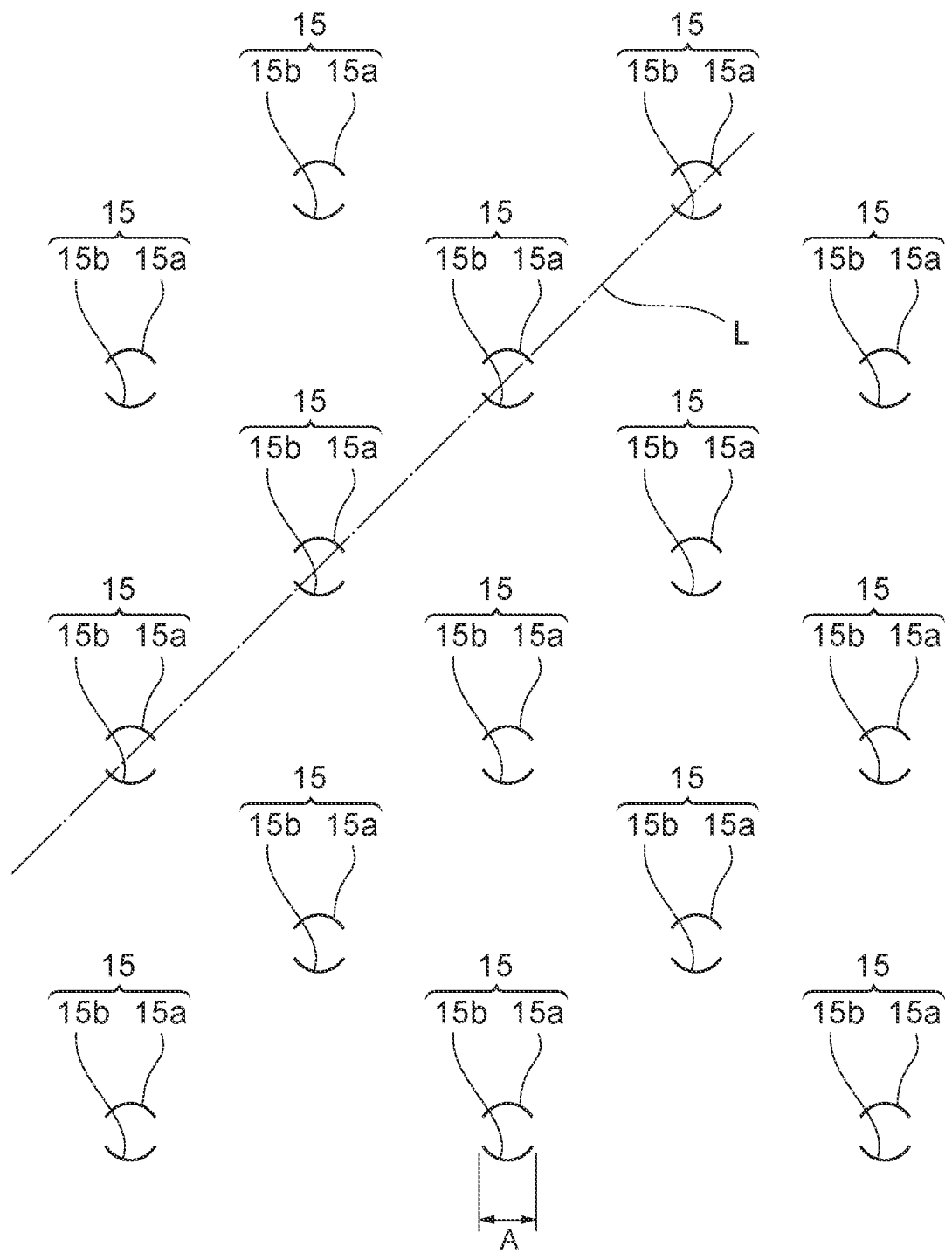
FIG. 5 is a plan view illustrating slits of the stretch material of FIG. 4.

FIG. 5 is a plan view of the stretch material 10 obtained by enlarging FIG. 4. As illustrated in FIGS. 4 and 5, the stretch material 10 has multiple first slits 15a and multiple second slits 15b. As one aspect, the first slits 15a and the second slits 15b penetrate through the skin layers 11a, 11b and the core layer 12. "Slits" indicate linear or curved notches formed in the stretch material. For example, the first slits 15a and the second slits 15b face each other in the width direction D1.

As one aspect, the first slits 15a are bent in a curved shape so as to protrude on one side in the width direction D1, while the second slits 15b are bent in a curved shape so as to protrude on the other side in the width direction D1. Moreover, the first slits 15a and the second slits 15b may be arc-shaped, stretching in the elongation direction (for example, the longitudinal direction D2). The fact that "the slits are arc-shaped, stretching in the elongation direction" indicates that at least part of the slits stretching in an arc shape are formed in the elongation direction. Note that either the first slits 15a or the second slits 15b may be omitted.

Hereinafter, the first slits 15a and the second slits 15b are collectively referred to as the slits 15. Each slit 15 is expanded when the stretch material 10 is elongated. Multiple slits 15 are discretely formed. Here, the fact that "the slits are discretely formed" includes the fact in which multiple slits are disposed so as to be dispersed without any continuation therebetween. Note that, at the very least, none of multiple slits 15 may penetrate through the skin layers 11a, 11b and the core layer 12.

As one example, multiple slits 15 are disposed in a staggered manner. Here, the fact that "the slits are disposed in a staggered manner" indicates that the arrangement of slits in which the virtual straight line L connecting one slit and another slit closest to the one slit are inclined in the width direction D1 and the longitudinal direction D2. As one example, multiple slits 15 are disposed so as to be substantially equally dispersed in the stretch material 10. The interval between one slit and another slit closest to the one slit (hereinafter, "the interval between the multiple slits"), for example, is 1.5 mm or larger and 2.5 mm or smaller. The fact that "multiple slits are disposed so as to be substantially equally dispersed," for example, includes the state in which multiple slits are disposed at positions so as to be symmetric with respect to a predetermined point or line, or the state in which multiple slits are disposed so as to be dispersed in a concentric shape.

When the slits 15 are disposed so as to be substantially equally dispersed, for example, the effects of causing uniform strength of the stretch material are exerted. Moreover, the slits 15 may be evenly disposed in the overall stretch material or may be locally disposed in the specific site of the stretch material. If the slits 15 are locally disposed, for example, in accordance with the kind of clothing product, the effects of controlling the permeability and strength at an appropriate position are exerted. In this way, the disposition aspect of the slits 15 can be appropriately changed. In one aspect, for example, the angle formed by the straight line L and the longitudinal direction D2, as well as the angle formed by and straight line L and the width direction D1, is 45°. Note that this angle can be appropriately changed.

Figure 6:
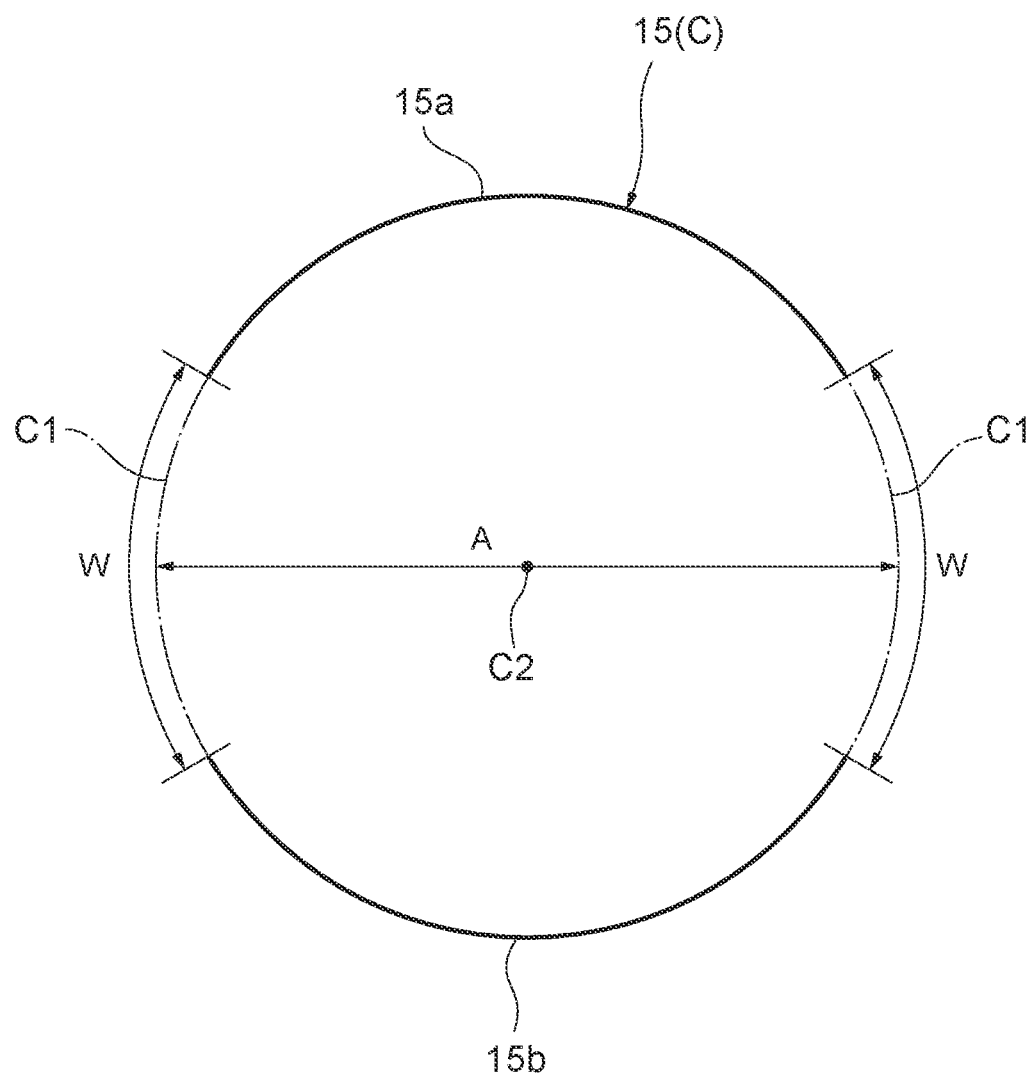
FIG. 6 is a plan view obtained by enlarging the slits of FIG. 5.
Figure 6:
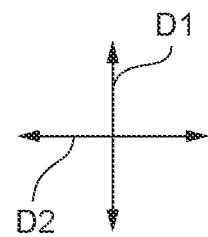

FIG. 6 is a plan view illustrating one enlarged slit 15. As illustrated in FIG. 6, as one example, both the first slit 15a and the second slit 15b are circular arc-shaped, stretching along the circumference of virtual circle C. For example, the first slit 15a, the second slit 15b, and unexcision parts C1 with slits not formed therein are provided in the circumference of virtual circle C, with one pair of unexcision parts C1 disposed in the longitudinal direction D2.

As mentioned above, the slits 15 are circular arc-shaped, and the diameter A of the slits 15, for example, is 0.3 mm or larger and 8 mm or smaller, preferably 0.3 mm or larger and 2 mm or smaller, more preferably 0.5 mm or larger and 1.5 mm or smaller. As the diameter A of the slits 15 increases, advantageously, the slits 15 are easily formed to achieve high manufacturability of the stretch material 10. Moreover, if the diameter A of the slits 15 is 0.3 mm or larger and 2 mm or smaller, the designability and aesthetically pleasing appearance of the arrangement of the slits 15 can be enhanced; in contrast, if the diameter A is 0.5 mm or larger and 1.5 mm or smaller, the abovementioned effects are further remarkable.

While the length W of each unexcision part C1 in the circumferential direction can be appropriately changed in accordance with the diameter of the slits 15, required permeability, and required physical properties, they are, for example, 0.5 mm or larger and 6.0 mm or smaller. Moreover, the length W in the circumferential direction of each unexcision part C1 may be 15% or higher and 25% or lower of the circumference of the virtual circle C. As one example, one pair of unexcision parts C1 are disposed at positions mutually symmetric with respect to the center C2 of the virtual circle C. The first slit 15a and the second slit 15b are also disposed at positions mutually symmetric with respect to the center C2. For example, the ratio of the area of multiple virtual circles C in the stretch material 10 is 0.5% or higher and 30% or lower.

Figure 7:
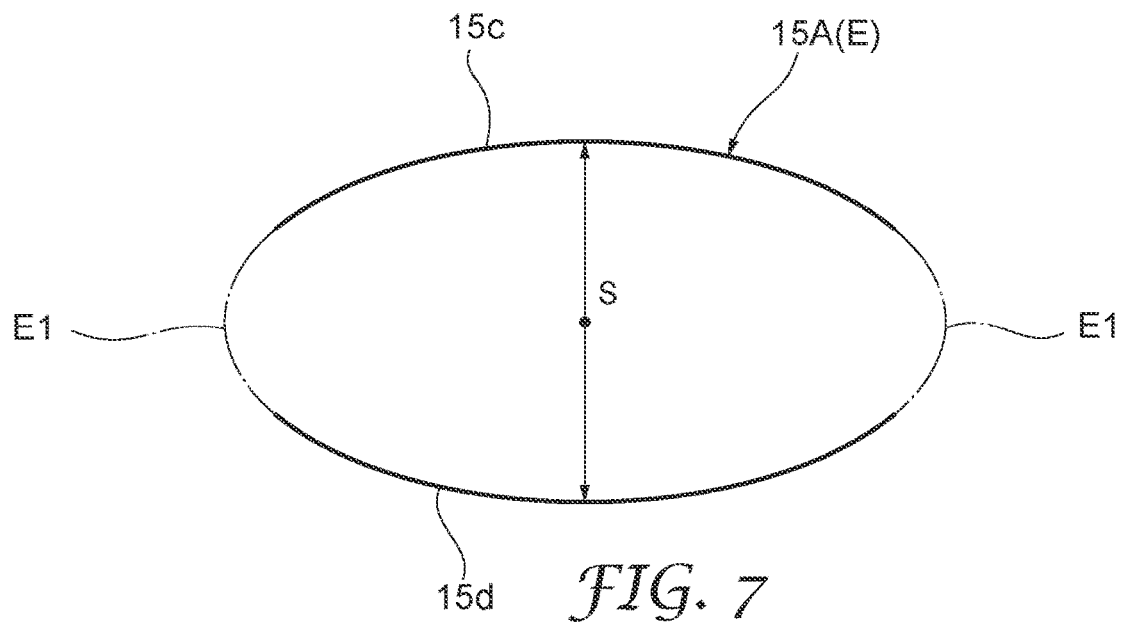
FIG. 7 is a plan view illustrating slits according to a modified example.

While the circular arc-shaped slits 15 have been described in the abovementioned example, the shape of the slits, for example, may be a linear shape, curved shape, sine wave shape, rectangular wave shape, mountain and valley shape, or other shapes, and can be appropriately changed. FIG. 7 illustrates a slit 15A including an elliptical arc-shaped third slit 15c and fourth slit 15d. Both the third slit 15c and the fourth slit 15d stretch along the circumference of virtual ellipse E, with the third slit 15c, the fourth slit 15d, and one pair of unexcision parts E1 disposed on the circumference of virtual ellipse E.

The long axis of the slit 15A and the length of the short axis thereof can be appropriately changed, and for example, the length of the short axis S of the slit 15A is 0.3 mm or larger and 8 mm or smaller. The length of the short axis S thereof is preferably 0.3 mm or larger and 2 mm or smaller, more preferably 0.5 mm or larger and 1.5 mm or smaller. As in the abovementioned slit 15, the longer the short axis S of the slit 15A is, the higher the stretch material has manufacturability. Further, if the short axis S thereof is 0.3 mm or larger and 2 mm or smaller, the designability and aesthetically pleasing appearance of the arrangement of the slit 15A can be enhanced; in contrast, if the short axis S thereof is 0.5 mm or larger and 1.5 mm or smaller, the abovementioned effects are further remarkable.

Figure 8:
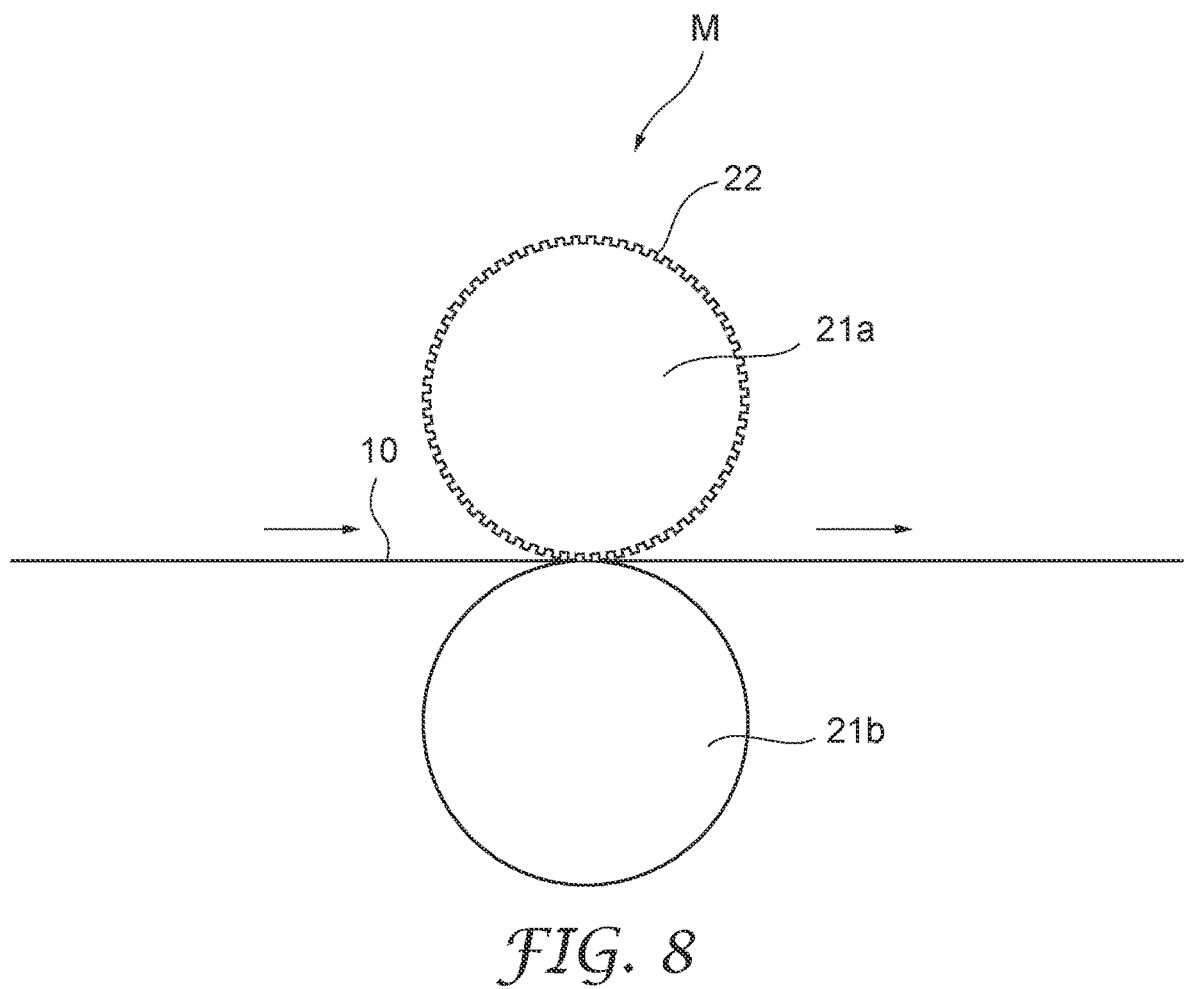
FIG. 8 is a side view illustrating one aspect of a means for forming slits.

FIG. 8 is a view illustrating one example of a manufacturing apparatus of the stretch material 10 including multiple slits. The manufacturing apparatus M of FIG. 8 includes: a first roll 21a including a die cutter 22; and a second roll 21b pressed by the first roll 21a. In the manufacturing method of the stretch material 10 according to one aspect, the stretch material 10 is transported while interposed between the first roll 21a and the second roll 21b, while the die cutter 22 is pressed against, pushes and cuts, or punches the stretch material 10 to form multiple slits. Moreover, instead of die cutting, a cutter and the stretch material 10 may be relatively moved to run the cutter and cut the stretch material 10. In this way, the manufacturing method of the stretch material 10 according to one aspect includes the step of forming multiple discretely formed slits by cutting the stretch material 10. Note that slits may be formed using lasers or ultrasonic waves; in this case, multiple slits may be formed under conditions in which the generation of projections and recesses caused by heat is suppressed (wavelength, frequency, temperature, etc.).

Moreover, if the transportation direction (MD: Machine Direction) in which the stretch material 10 is transported corresponds to the width direction D1, and the orthogonal direction (CD: Cross Direction) of the transportation direction of the stretch material 10 corresponds to the longitudinal direction D2, the slits may be expanded in CD using a ring roll, gear roll, crown roll, tenter, etc. In contrast, if the transportation direction (MD: Machine Direction) in which the stretch material 10 is transported corresponds to the longitudinal direction D2, and the orthogonal direction (CD: Cross Direction) of the transportation direction of the stretch material 10 corresponds to the width direction D1, the slits may be expanded in MD by changing the speed of the roll such as a ring roll, gear roll, or crown roll.

The stretch material 10 serves as a stretchable member, for example, when subjected to stretching in the longitudinal direction D2. The elongation rate of the stretch material 10, for example, is 150% or higher, preferably 200% or higher, more preferably 400% or higher, further preferably 500% or higher when it is elongated in at least one direction (for example, the longitudinal direction D2). The tensile strength of the stretch material 10, for example, is 1 N/25 mm or higher, preferably 3 N/25 mm or higher, more preferably 5 N/25 mm or higher, further preferably 7/25 mm or higher when it is elongated in at least one direction.

The tensile yield stress in one direction of the skin layers 11a and 11b, for example, is mutually substantially the same. When the stretch material 10 is stretched in one direction, the skin layers 11a and 11b are plastically deformed to form a stretch part. The tensile stress of the stretch material 10 at 300% elongation in the longitudinal direction D2, for example, is 110% or lower of the tensile yield stress of the skin layer 11a and the tensile yield stress of the skin layer 11b. As a result, even when practically useful elongation of approximately 200% is carried out, the shape retaining part can maintain the original shape and favorable bondability to other members is maintained.

Figure 9A:
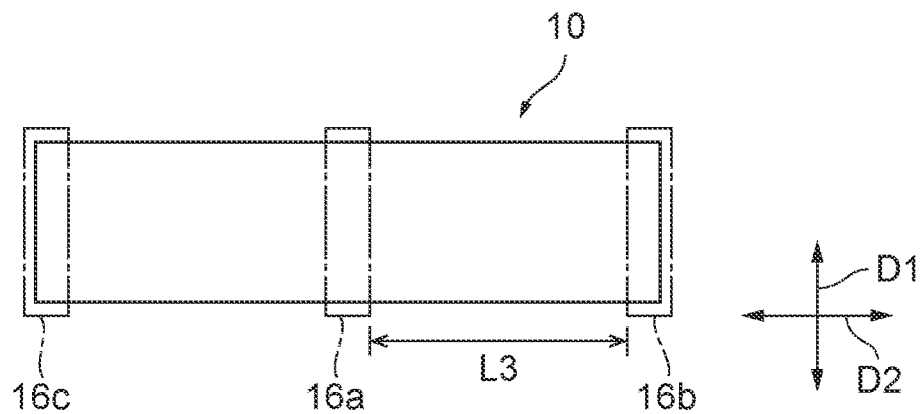
FIGS. 9A and 9B are views describing one aspect of stretching of the stretch material.
Figure 9B:
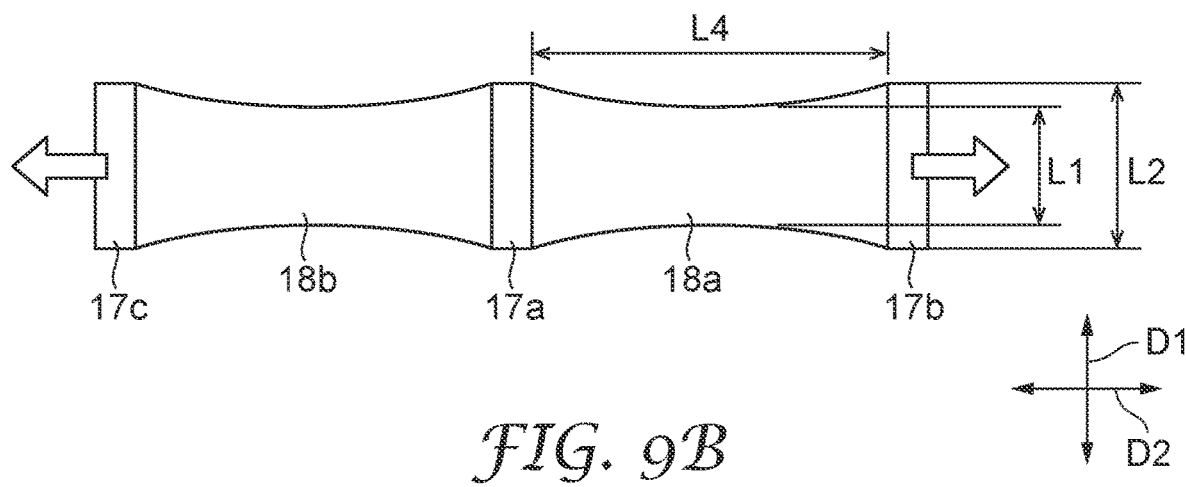

FIGS. 9A and 9B are views describing one aspect of stretching of the stretch material 10. In the present embodiment, a central region 16a and both end regions 16b, 16c in the longitudinal direction D2 of the stretch material 10 are held by a holding member, the region 16a is fixed, and the regions 16b, 16c are pulled in the longitudinal direction D2 so as to stretch between the regions 16a and 16b as well as between the regions 16a and 16c. The abovementioned slits may or may not be formed in the regions 16a, 16b, and 16c.

FIG. 9B illustrates the stretch material when stretched. As illustrated in FIG. 9B, shape retaining parts 17a, 17b, 17c are respectively formed in the regions 16a, 16b, and 16c held by a holding member. The shape retaining parts 17a, 17b, 17c are sites in which the shape of the stretch material 10 is maintained.

In contrast, a stretched part 18a is disposed between the regions 16a and 16b, while a stretched part 18b is disposed between the regions 16a and 16c. The stretched parts 18a, 18b correspond to sites in which the stretch material 10 is stretched. In the stretched parts 18a, 18b, the skin layers 11a, 11b of the stretch material 10 are plastically deformed.

Here, the contraction percentage in the width direction D1 was measured when it was elongated by 200% in the longitudinal direction D2. "The contraction percentage" indicates the ratio (L2–L1) of the contracted width to the width L2 before elongation, that is, the ratio (L2–L1)/L2 obtained by subtracting the minimum value L1 of the width during elongation from the width L2 before elongation. Moreover, "200% elongation" indicates that the length L4 during elongation to the initial length L3 of the elongated part is 200%.

Figure 10:
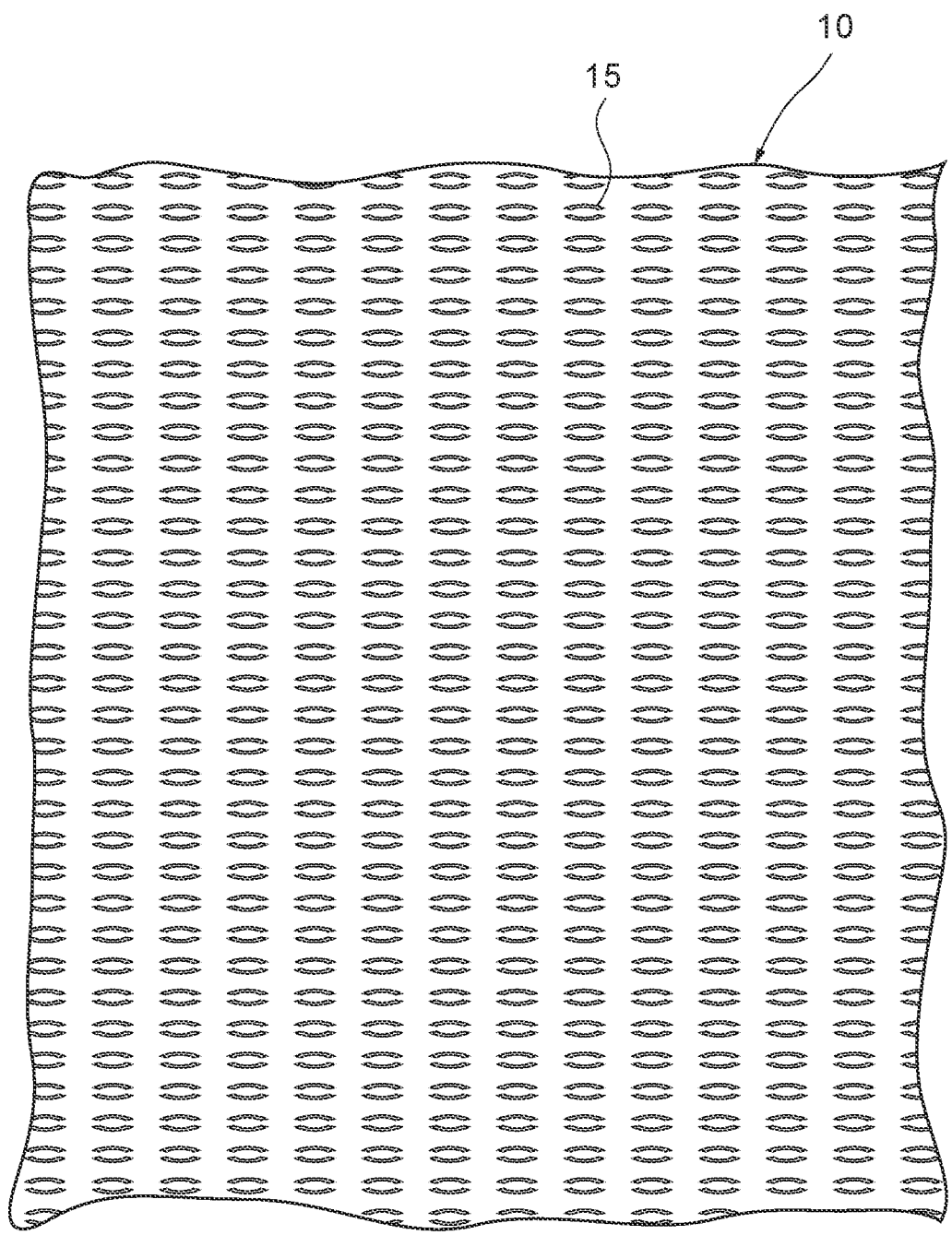
FIG. 10 is a view illustrating one aspect of slits expanded by stretching of the stretch material.
Figure 10:
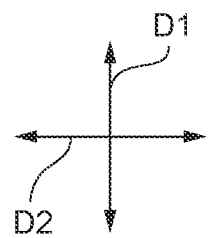

FIG. 10 is a plan view illustrating the stretch material 10 during elongation. As illustrated in FIG. 10, the expanded slits 15, for example, stretch long in the elongation direction (longitudinal direction D2), in addition to extending in the orthogonal direction (width direction D1) of the elongation direction. Therefore, in comparison with before elongation, because the expanded slits 15 are extended in the elongation direction and the orthogonal direction thereof, a stretchable member with enhanced permeability is manufactured.

When the stretch material is elongated to expand each slit 15, the permeability of the stretch material, for example, may be 10 (cm$^3$/cm$^2$·s) or higher, preferably 20 (cm$^3$/cm$^2$·s) or higher, more preferably 50 (cm$^3$/cm$^2$·s) or higher, further preferably 65 (cm$^3$/cm$^2$·s) or higher, remarkably preferably 80 (cm$^3$/cm$^2$·s) or higher. Moreover, before elongating the stretch material, the permeability of the stretch material 10 including the slits 15 may be 0 (cm$^3$/cm$^2$·s) or higher and lower than 10 (cm$^3$/cm$^2$·s).

Figure 11:
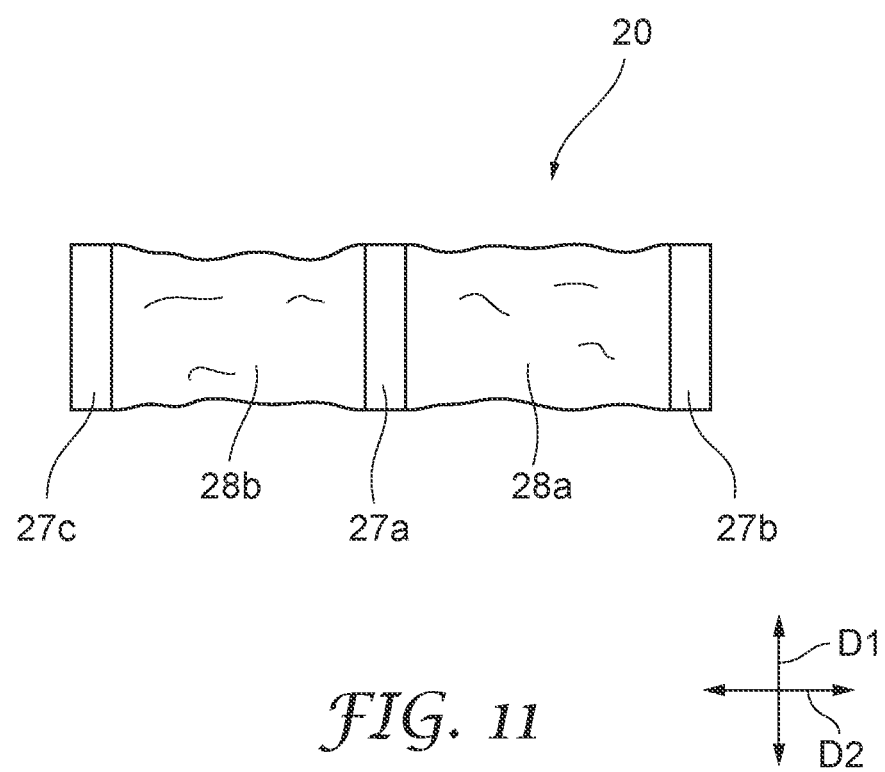
FIG. 11 is a plan view illustrating one aspect of a stretchable member according to an embodiment.

FIG. 11 is a plan view illustrating a stretchable member 20 according to one aspect. The stretchable member 20 includes: shape retaining parts 27a, 27b, 27c in which the layer structure of the stretch material 10 is maintained; and stretch parts 28a, 28b formed between the shape retaining parts 27a, 27b, 27c. When the stretchable member 20 is elongated in the longitudinal direction D2, the stretch parts 28a, 28b are elongated, while the shape of the shape retaining parts 27a, 27b, 27c is maintained. Therefore, when the stretchable member 20 is bonded to other members between the shape retaining parts 27a, 27b, 27c, favorable adhesion to other members is obtained.

Incidentally, if slits are formed in the regions 16a, 16b, and 16c held by the abovementioned holding member, slits are formed in the shape retaining parts 27a, 27b, 27c and the stretch parts 28a, 28b in the stretchable member 20. In contrast, if slits are not formed in the regions 16a, 16b, and 16c, in the stretchable member 20, slits are formed in the stretch parts 28a, 28b, while slits are not formed in the shape retaining parts 27a, 27b, 27c.

In terms of manufacturability, because slits can be collectively formed in all sites, slits are preferably formed in the shape retaining parts 27a, 27b, 27c and the stretch parts 28a, 28b. However, in terms of adhesion to other members, because fewer slits enhances adhesion, slits are preferably not formed in the shape retaining parts 27a, 27b, 27c.

Figure 12:
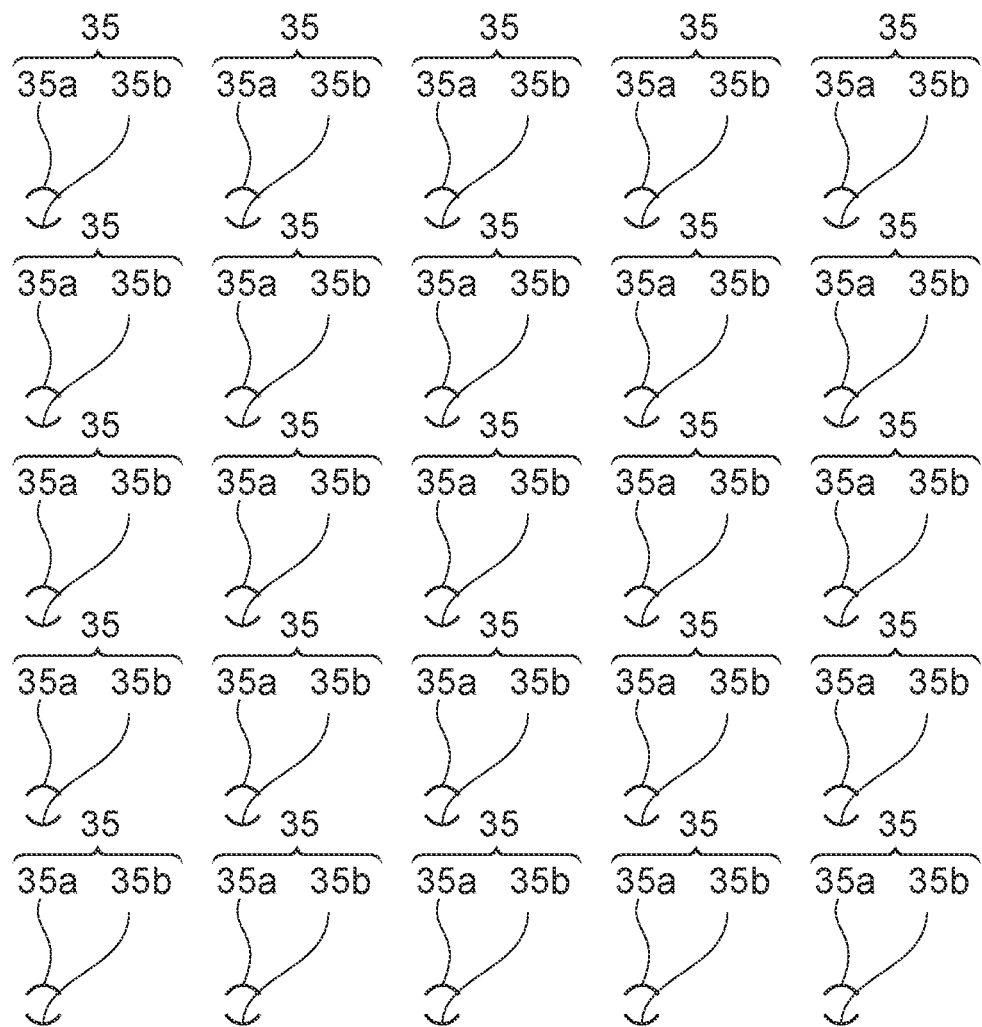
FIG. 12 is a plan view illustrating slits arranged differently from those of FIG. 5.
Figure 12:
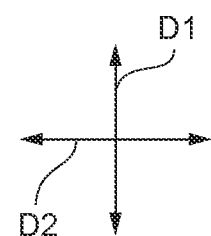

FIG. 12 is a plan view illustrating slits 35 according to another aspect formed in the stretch material. As in the slits 15, each slit 35 includes a first slit 35a and a second slit 35b. As illustrated in FIG. 12, multiple slits 35 are disposed in a lattice shape. Here, the fact that "slits are disposed in a lattice shape" indicates that the arrangement of slits in which the virtual straight line connecting one slit and another slit closest to the one slit coincides in the longitudinal direction D2 or the width direction D1.

FIG. 12 illustrates an example in which mutually adjacent four slits 35 form a square shape. If the mutually adjacent four slits 35 form a square shape, the strength in the longitudinal direction D2 and the width direction D1 can be kept uniform, making a square shape preferable. However, the shape formed by the mutually adjacent four slits may be other shapes such as a rectangle. In this way, the disposition aspect of the slits can be appropriately changed.

Next, the operational effects of the stretch material, stretchable member, and clothing product according to the embodiments will be described.

In the abovementioned embodiments, because the stretch material has multiple discretely formed slits 15, 15A, 35, permeability can be enhanced. Moreover, the formation of the slits 15, 15A, 35 tends not to form minute projections and recesses in the stretch material, enabling the creation of a stretch material having little roughness. Further, when the slits 15, 15A, 35 are formed, waste generated in the formation of perforations can be suppressed.

Moreover, if circular through holes, etc. are formed in the stretch material, in pasting the stretch material, etc., the adhesive presumably passes through the through holes, leading to the adhesion of an adhesive to a transportation device, etc. In contrast, like the embodiments, if the stretch material includes the slits 15, 15A, 35, because the passage of the adhesive can be suppressed, the adhesion of the adhesive to a transportation device, etc. can be suppressed.

The slits 15, 15A, 35 may be arc-shaped. If the slits 15, 15A, 35 are bent, when the stretch material is elongated, splits from the slits 15, 15A, 35 tend not to be generated. Moreover, the formation of the arc-shaped slits 15, 15A, 35 enables the suppression of flapping of parts in which the slits 15, 15A, 35 of the stretch material are formed.

The slits 15, 15A, 35 may be arc-shaped, stretching in the elongation direction (longitudinal direction D2). As a result, when the stretch material is elongated in the elongation direction, the slits 15, 15A, 35 tend not to be excessively opened. Therefore, when the stretch material is elongated in the elongation direction, splits from the slits 15 can be suppressed; accordingly, the durability of the stretch material can be enhanced when it is elongated in the elongation direction.

The slits 15, 15A, 35 may be circular arc-shaped or elliptical arc-shaped and the diameter A of the slits 15, 15A, 35 or the length of the short axis S thereof may be 0.3 mm or larger and 8 mm or smaller. Because the slits 15, 15A, 35 have a circular arc-shape or elliptical arc-shape with no corners, breaks tend not to be generated from the slits 15, 15A, 35. Moreover, when the diameter A or the short axis S of the slits 15, 15A, 35 is 0.3 mm or larger and 8 mm or smaller, the aesthetically pleasing appearance of the stretch material with the multiple slits 15, 15A, 35 formed therein can be enhanced.

The stretch material 10 may include: a core layer 12 including an elastomer; and the skin layers 11a, 11b provided on the primary surface of the core layer 12, wherein the slits 15, 15A, 35 may penetrate through the core layer 12 and the skin layers 11a, 11b. As a result, because the slits 15, 15A, 35 penetrate through the core layer 12 and the skin layers 11a, 11b, the core layer 12 and skin layers 11a, 11b having high permeability can be obtained.

The slits 15, 15A, 35 may be expanded when the stretch material is elongated. As a result, because the slits 15, 15A, 35 are expanded during elongation of the stretch material, higher permeability can be obtained during elongation.

In the stretch material 10, the permeability may be 10 (cm$^3$/cm$^2$·s) or higher when the slits 15, 15A, 35 are expanded. As a result, high permeability can be obtained.

In the stretch material 10, the tensile stress at second 150% elongation may be 2 N/25 mm or lower. As a result, a clothing product such as a diaper 1, including the stretch material 10 can be easily elongated when worn.

In the stretch material 10, the recovery stress at second 250% elongation may be 0.2 N/25 mm or higher. As a result, after wearing the clothing product such as a diaper 1 including the stretch material 10, mechanical properties suitable for being fit for the human body can be obtained.

In the stretch material 10, the elongation rate may be 150% or higher when it is elongated in at least one direction (for example, the longitudinal direction D2). As a result, in the state in which multiple slits 15, 15A, 35 are formed, a high elongation rate can be maintained.

In the stretch material 10, the tensile strength may be 1 N/25 mm or higher when it is elongated in at least one direction. As a result, in the state in which multiple slits 15, 15A, 35 are formed, high tensile strength can be maintained.

The manufacturing method of the stretch material 10 may include the step of forming the multiple discretely formed slits 15, 15A, 35 by cutting the stretch material 10. In this manufacturing method of the stretch material 10, because multiple discretely disposed slits 15, 15A, 35 can be formed in the stretch material 10, the same operational effects as in the stretch material 10 can be obtained.

The stretchable member 20 includes: stretch parts 28a, 28b having a structure in which the skin layers 11a, 11b of the stretch material 10 are plastically deformed; and shape retaining parts 27a, 27b, 27c by which the layer structure of the stretch material 10 is maintained. Because the stretchable member 20 includes the stretch material 10, the same operational effects as in the stretch material 10 can be obtained. Moreover, if the stretchable member 20 is applied to a clothing product such as a diaper 1, the stretch parts 28a, 28b are elongated when worn, with the shape of the shape retaining parts 27a, 27b, 27c maintained. Therefore, because it can be bonded to other members in the shape retaining parts 27a, 27b, 27c, favorable bondability to other members is obtained.

The diaper 1 includes the stretch material 10 or the stretchable member 20. Therefore, in the diaper 1, the same operational effects as in the abovementioned stretch material 10 or stretchable member 20 can be obtained.

As mentioned above, while the embodiments of the present invention have been described, the present invention is not limited to the abovementioned embodiments.

EXAMPLES

Next, examples of the stretch material and stretchable member will be described. The present invention is not limited to the below-mentioned examples. In the experiment according to the examples, as mentioned below, the stretch materials of Examples 1 to 12, the stretch materials of Reference Examples 1, 2, and the stretch material of Comparative Example 1 were subjected to tensile testing to measure the permeability, tensile stress, elongation rate, generation amount of waste in forming slits, etc., the presence of odor of rubber, etc. in forming slits, etc., the presence of the passage of the adhesive to slits, etc. Measurements were made such that permeability testing was in accordance with JIS L 1096, while tensile testing was in accordance with JIS K 7127 (width of a test piece: 25 mm, interval between chucks: 50 mm, speed of the test: 300 mm/min).

As the materials of Examples 1 to 12, Reference Examples 1, 2, and Comparative Example 1, the following materials were commonly used. As the resin material making up the core layer, a mixture material was used which was obtained by mixing 40 parts by mass of "Quantac 3620" (manufactured by Zeon Corporation, styrene-isoprene-styrene block copolymer, a mixture of linear polymers and branched polymers), 56 parts by mass of "Quintac 3390" (manufactured by Zeon Corporation, styrene-isoprene-styrene block copolymers, linear polymers), and 4 parts by mass of styrene-isoprene-styrene block copolymer-based white masterbatch containing 20% $TiO_2$. Note that a white masterbatch is added to color it white. Moreover, as the resin material making up the skin layer, "Novatec PP FA3EB" (manufactured by Japan Polypropylene Corporation, polypropylene homopolymer) was used. The ratio of the thickness of the skin layer:core layer:skin layer was configured to be 15:75:15 (the ratio of the thickness of the skin layer to the thickness of the core layer was 0.43). The total thickness of the three layers was approximately 37 μm. Moreover, in Examples 1 to 12, Reference Examples 1, 2, and Comparative Example 1, the transportation direction (MD: Machine Direction) in which the stretch material 10 was transported corresponded to the width direction D1, while the orthogonal direction (CD: Cross Direction) of the transportation direction of the stretch material 10 corresponded to the longitudinal direction D2.

Example 1

In Example 1, as illustrated in FIG. 13A, multiple slits including circular arc-shaped first slits and second slits stretching in the longitudinal direction D2 were disposed in a staggered manner, the diameter A1 was 1 mm, the length W1 of each unexcision part was 0.6 mm, and the interval between the multiple slits was 2 mm.

Example 2

In Example 2, as illustrated in FIG. 13B, multiple slits including circular arc-shaped first slits and second slits stretching in the longitudinal direction D2 were disposed in a staggered manner, the diameter A2 was 1.3 mm, the length W2 of each unexcision part was 0.6 mm, and the interval between the multiple slits was 2 mm.

Example 3

In Example 3, as illustrated in FIG. 13C, multiple slits including circular arc-shaped first slits, second slits, and third slits stretching in the longitudinal direction D2 were disposed in a staggered manner, the diameter A3 was 1 mm, the length W3 of each unexcision part was 0.6 mm, and the interval between the multiple slits was 2 mm.

Example 4

In Example 4, as illustrated in FIG. 13D, multiple slits including circular arc-shaped first slits and second slits stretching in the width direction D1 were disposed in a staggered manner, the diameter A4 was 1 mm, the length W4 of each unexcision part was 0.6 mm, and the interval between the multiple slits was 2 mm.

Example 5

In Example 5, as illustrated in FIG. 13E, multiple slits stretching in a semicircle shape in the width direction D1 were disposed in a staggered manner, the diameter A5 was 1 mm, and the interval between the multiple slits was 2 mm.

Example 6

In Example 6, the same multiple slits as in Example 1 were disposed in a lattice shape and the interval between the multiple slits was 1.9 mm.

Example 7

In Example 7, in the virtual circle illustrated in FIG. 13B, slits having a diameter A2 of 1.5 mm were disposed in a staggered manner, the length W2 of each unexcision part was 0.6 mm, and the interval between the multiple slits was 2 mm.

Example 8

In Example 8, in the virtual circle illustrated in FIG. 13B, slits having a diameter A2 of 1.3 mm were disposed in a lattice shape, the length W2 of each unexcision part was 0.6 mm, and the interval between the multiple slits was 2.8 mm.

Example 9

In Example 9, in the virtual circle illustrated in FIG. 13B, slits having a diameter A2 of 6 mm were disposed in a staggered manner, the length W2 of each unexcision part was 0.6 mm, and the interval between the multiple slits was 12 mm.

Example 10

In Example 10, as illustrated in FIG. 13F, multiple slits including first slits and second slits linearly stretching obliquely in both the width direction D1 and the longitudinal direction D2 to create a cross shape were disposed in a staggered manner, the length A6, A7 of the first slits and the second slits was 1 mm, and the interval between the multiple slits was 2 mm.

Example 11

In Example 11, as illustrated in FIG. 13G, linear slits stretching in the longitudinal direction D2 were disposed in a staggered manner, the length A8 was 1 mm, and the interval between the multiple slits was 2 mm.

Example 12

In Example 12, as illustrated in FIG. 13H, linear slits stretching in the width direction D1 were disposed in a staggered manner, the length A9 was 1 mm, and the interval between the multiple slits was 2 mm.

Reference Example 1

In Reference Example 1, as illustrated in FIG. 13I, multiple circular through holes were disposed in a staggered manner by die cutting, the diameter A10 was 1 mm, the interval between the multiple through holes was 2 mm.

Reference Example 2

In Reference Example 2, as illustrated in FIG. 13J, multiple circular through holes were disposed in a lattice shape using heated needles, the diameter A11 was 0.62 mm, and the interval between the multiple through holes was 1.5 mm.

Comparative Example 1

In Comparative Example 1, a stretch material having neither slits nor through holes was used.

The results of the tensile testing carried out in the above-mentioned Examples 1 to 12, Reference Examples 1, 2, and Comparative Example 1 are described in the below-mentioned Tables 1 and 2. Note that Tables 1 and 2 indicate the permeability, stress at break, elongation rate at break, tensile stress at break, before and after elongating and activating the stretch material; the presence of the generation of waste; the presence of the generation of a rubber odor, etc.; and the presence of passage of the adhesive. Note that regarding the presence of the generation of waste, the presence of the generation of odor, and the presence of passage of the adhesive, those remarkably generated were regarded as "Yes,", while those not remarkably generated (including the generation of a small amount) were regarded as "No." In Tables 1 and 2, "D1" indicates direction D1 (transportation direction (MD: Machine Direction) in which the stretch material is transported), while "D2" indicates direction D2 (the orthogonal direction (CD: Cross Direction) of the transportation direction of the stretch material).

TABLE 1

| | | Example 1 | Example 2 | Example 3 | Example 4 | Example 5 | Example 6 | Example 7 |
|---|---|---|---|---|---|---|---|---|
| Before activation | Permeability ($cm^3/cm^2 \cdot s$) | 0 | 0 | 0 | 0 | 0 | 0 | 0 |
| | D1 Stress at break (N) | 6.5 | 5.25 | 7.5 | 9.4 | 8.1 | 5.4 | 5 |
| | D1 Elongation rate at break (%) | 169 | 177 | 181 | 364 | 259 | 157 | 224 |
| | D2 Tensile stress at break (N) | 9 | 9.35 | 7.4 | 5.5 | 4.7 | 8.1 | 7.6 |
| | D2 Elongation rate at break (%) | 722 | 880 | 593 | 514 | 441 | 670 | 834 |
| After activation | Permeability ($cm^3/cm^2 \cdot s$) | 37 | 126 | 11 | 25 | 32 | 115 | 149 |
| | D1 Stress at break (N) | 6.5 | 4.7 | 6 | 9.2 | 7.3 | 6.2 | 4.7 |
| | D1 Elongation rate at break (%) | 260 | 250 | 92 | 320 | 223 | 280 | 250 |
| | D2 Tensile stress at break (N) | 7.7 | 5.6 | 4.2 | 4.6 | 4.2 | 6.8 | 5.6 |
| | D2 Elongation rate at break (%) | 648 | 691 | 161 | 408 | 328 | 610 | 691 |
| Generation of waste | | No | No | No | No | No | No | No |
| Generation of odor | | No | No | No | No | No | No | No |
| Passage of the adhesive | | No | No | No | No | No | No | No |

TABLE 2

| | | Example 8 | Example 9 | Example 10 | Example 11 | Example 12 | Reference Example 1 | Reference Example 2 | Comparative Example 1 |
|---|---|---|---|---|---|---|---|---|---|
| Before activation | Permeability ($cm^3/cm^2 \cdot s$) | 0 | 1.1 | 0 | 0 | 0 | 77 | 89 | 0 |
| | D1 Stress at break (N) | 5.6 | 5.2 | 6.6 | 5.1 | 15 | 8.5 | 8.4 | 13 |
| | D1 Elongation rate at break (%) | 150 | 141 | 157 | 131 | 631 | 320 | 360 | 716 |
| | D2 Tensile stress at break (N) | 7.6 | 9.5 | 5.3 | 15.8 | 4 | 9.2 | 6.2 | 14.2 |
| | D2 Elongation rate at break (%) | 724 | 786 | 512 | 916 | 18.3 | 808 | 756 | 1100 |
| After activation | Permeability ($cm^3/cm^2 \cdot s$) | 116 | 95 | 30 | 26 | 25 | 130 | 137 | 0 |
| | D1 Stress at break (N) | 5.7 | 6.2 | 6.8 | 4 | 11.8 | 6.7 | 7 | 9.1 |
| | D1 Elongation rate at break (%) | 212 | 211 | 217 | 73 | 443 | 281 | 258 | 352 |
| | D2 Tensile stress at break (N) | 8.1 | 11 | 4.5 | 11 | 3 | 8.7 | 5.8 | 14.8 |
| | D2 Elongation rate at break (%) | 737 | 797 | 400 | 707 | 167 | 764 | 676 | 1000 |
| Generation of waste | | No | No | No | No | Yes | No | No | No |
| Generation of odor | | No | No | No | No | No | No | Yes | No |
| Passage of the adhesive | | No | No | No | No | No | Yes | Yes | No |

As indicated in Tables 1 and 2, before activation, the permeability was 0 except for Example 9 as well as Reference Examples 1, 2 in which circular through holes were formed. However, after activation, permeability higher than 0 was obtained except for Comparative Example 1 which had neither slits nor through holes. In particular, in Example 2, permeability (126 (cm$^3$/cm$^2$·s)) as high as in Reference Examples 1, 2 with through holes formed therein was obtained, while in Example 7 in which the diameter A2 was 1.5 mm, permeability (149 (cm$^3$/cm$^2$·s)) of Reference Examples 1, 2 or higher was obtained. Note that in comparison with Example 10 with cross-shaped slits disposed therein, flapping from the part in which slits were formed was able to be suppressed in Examples 1 to 9. Moreover, it has been found that in comparison with Example 11 in which slits linearly stretching in the elongation direction (direction D2) were disposed, the stress at break in direction D1 and the elongation rate at break in direction D1 was able to be increased in Examples 1 to 10, 12. Further, it has been found that in comparison with Example 12 in which slits linearly stretching in the orthogonal direction (direction D1) of the elongation direction were disposed, the tensile stress at break in direction D2 was able to be increased in Examples 1 to 11.

Moreover, regarding the generation of waste, while waste was remarkably generated in Reference Example 1 in which perforations were formed by die cutting, in Examples 1 to 12, Reference Example 2, and Comparative Example 1, the generation of waste was not remarkable. Regarding the presence of the generation of a rubber odor, etc., such odor was remarkably generated in Reference Example 2 in which through holes were formed using heated needles, but not remarkably generated in Examples 1 to 12, Reference Example 1, and Comparative Example 1. The passage of the adhesive was remarkable in Reference Examples 1, 2 in which through holes were formed, while in Examples 1 to 12 and Comparative Example 1, the passage of the adhesive was not remarkable.

As mentioned above, it has been found that in Examples 1 to 12 in which slits were formed, permeability was able to be assured, while the generation of waste, the generation of odor of rubber, etc., and the passage of the adhesive were able to be suppressed. Moreover, FIG. 14 illustrates one example of the relationship between the elongation rate and tensile stress in the stretch materials and stretchable members according to Examples 1 to 6, 10 and Reference Examples 1, 2.

Figure 14:
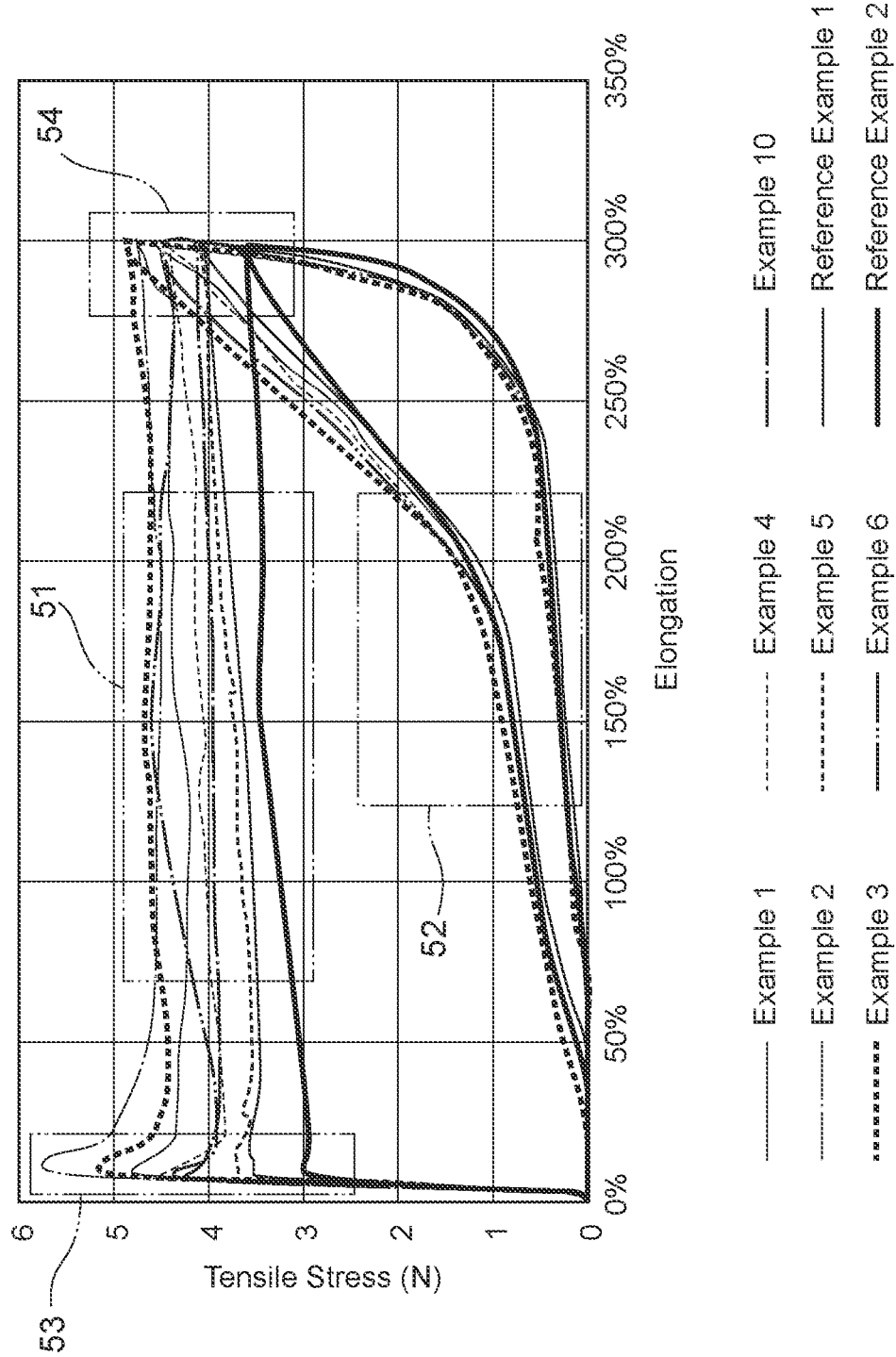
FIG. 14 is a view illustrating one example of the relationship between the elongation rate and tensile stress in the stretch materials according to the examples and reference examples.

In FIG. 14, each line passing within region 51 indicates the relationship between the elongation rate and tensile stress in elongating the stretch material. Each line passing within region 52 indicates the relationship between the elongation rate and tensile stress in the stretchable member obtained by elongating the stretch material by 300%. Each top positioned within region 53 indicates the tensile yield point of the skin layer in each stretch material, with the tensile stress of each top corresponding to the tensile yield stress of the skin layer. Each top positioned within region 54 indicates the tensile stress of each stretch material at 300% elongation. It has been found that as illustrated in FIG. 14, the stretch materials and stretchable members of Examples 1 to 6, 10 had a higher ratio of the elongation rate to the tensile stress than the stretch materials and stretchable members of Reference Examples 1, 2. Moreover, it has been found that the stretch materials and stretchable members of Examples 1 to 6, 10 had a higher tensile yield point (tensile yield stress) of the skin layer in each stretch material and higher tensile stress at 300% elongation than those of the stretch materials and stretchable members of Reference Examples 1, 2.

1 Diaper (clothing product)
10 Stretch material
11a, 11b Skin layers
12 Core layer
15, 15A, 35 Slits
20 Stretchable member
22 Die cutter
27a, 27b, 27c Shape retaining parts
28a, 28b Stretch parts
A Diameter
S Short axis.

What is claimed:

1. A stretch material including an elastomer and having multiple discretely formed slits, comprising
   a core layer including the elastomer; and a skin layer provided on at least one primary surface of the core layer,
   wherein the slits penetrate through the core layer and the skin layer,
   wherein the slits are circular or elliptical-arc shaped, wherein the slits are expanded when the stretch material is elongated, maintaining an arc-shape while being stretched in an elongation direction, and
   wherein the circular or elliptical arc-shaped slits each comprises a first curved slit and a second curved slit provided in a circumference of a virtual circle or ellipse along with unexcision parts not having slits formed therein between ends of the first curved slit and the second curved slit, wherein the stretch material is continuous within the virtual circle or ellipse.

2. The stretch material according to claim 1, wherein an air permeability of the stretch material is 10 cm$^3$/cm$^2$ or higher when the slits are expanded.

3. The stretch material according to claim 2, wherein the air permeability is 0 cm$^3$/cm$^2$ or higher and lower than 10 cm$^3$/cm$^2$ prior to the slits being expanded.

4. The stretch material according to claim 2, wherein the air permeability is 80 cm$^3$/cm$^2$ or higher when the slits are expanded.

5. The stretch material according to claim 1, wherein the stretch material comprises a longitudinal length and a width less than the length, wherein a first curved slit is curved such that it protrudes toward a first width side and the second curved slit is curved such that it protrudes toward an opposing second width side.

6. The stretch material according to claim 5, wherein the elongation direction is a longitudinal direction parallel to a first width side and a second width side.

7. The stretch material according to claim 1, wherein the diameter of the virtual circle or the dimension of the short axis of the virtual ellipse is 0.3 mm or larger and 8 mm or smaller.

8. The stretch material according to claim 7, wherein the diameter is 0.5 mm or larger and 1.5 mm or smaller.

9. The stretch material according to claim 1, wherein the circumferential length of each unexcision part is 15% or higher and 25% or lower of the circumference of the virtual circle or ellipse.

10. The stretch material according to claim 1, wherein an area ratio of multiple virtual circles or ellipses is 0.5% or higher and 30% or lower.

11. The stretch material according to claim 1, wherein a tensile stress at second 150% elongation is 2 N/25 mm or lower.

12. The stretch material according to claim 1, wherein a recovery stress at second 250% elongation is 0.2 N/25 mm or higher.

13. The stretch material according to claim 1, wherein an elongation rate is 150% or higher when the stretch material is elongated in the elongation direction.

14. The stretch material according to claim 1, wherein a tensile strength is 1 N/25 mm or higher when the stretch material is elongated in the elongation direction.

15. The stretch material according to claim 1, wherein the 10% tensile stress of the core layer is higher than the 10% tensile stress of the skin layer, wherein the 10% tensile stress of the core layer is 0.5 MPa or lower and the 10% tensile stress of the skin layer is 1 MPa or higher and 15 MPa or lower.

16. A manufacturing method of a stretch material according to claim 1, comprising:
   a step of forming multiple discretely formed slits by cutting the stretch material.

17. A stretchable member comprising the stretch material according to claim 1, wherein the core layer and the skin layer on at least one primary surface of the core layer form a layer structure, the stretchable member comprising:
   at least one stretch part in which the skin layer of the layer structure is plastically deformed when the stretch material is elongated; and
   at least one shape retaining part by which a shape of the layer structure of is maintained when the stretch material is elongated.

18. The stretchable member according to claim 17, wherein the stretchable member comprises a longitudinal length and a width less than the length, and wherein upon elongation in a longitudinal direction the width of the at least one stretch part narrows and the width of the at least one shape retaining part is kept constant.

19. A clothing product, comprising the stretch material according to claim 1.

20. The clothing product according to claim 14, wherein the clothing product is a diaper and a nonwoven fabric is laminated on both primary surfaces of the stretch material.

* * * * *

UNITED STATES PATENT AND TRADEMARK OFFICE
CERTIFICATE OF CORRECTION

| | | |
|---|---|---|
| PATENT NO. | : 11,390,052 B2 | Page 1 of 1 |
| APPLICATION NO. | : 15/733111 | |
| DATED | : July 19, 2022 | |
| INVENTOR(S) | : Kenichiro Morishita | |

It is certified that error appears in the above-identified patent and that said Letters Patent is hereby corrected as shown below:

In the Claims

<u>Column 24</u>
Line 17 (approx.), In Claim 20, delete "claim 14" and insert -- claim 19 --, therefor.

Signed and Sealed this
Fourth Day of April, 2023

Katherine Kelly Vidal
*Director of the United States Patent and Trademark Office*